US006500923B1

(12) United States Patent
Seelig et al.

(10) Patent No.: US 6,500,923 B1
(45) Date of Patent: *Dec. 31, 2002

(54) DERMATOMYOSITIS-SPECIFIC AUTO-ANTIGEN

(75) Inventors: Hans Peter Seelig, Karlsruhe; Manfred Renz, Heidelberg, both of (DE)

(73) Assignee: Privates Institut fur Immunologie und Molekulargenetik GmbH, Karlsruhe (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/158,707

(22) Filed: Sep. 22, 1998

Related U.S. Application Data

(62) Division of application No. 08/913,832, filed as application No. PCT/DE96/00444 on Mar. 8, 1996, now Pat. No. 6,329,517.

(30) Foreign Application Priority Data

Mar. 15, 1995 (DE) .......................................... 195 09 279

(51) Int. Cl.[7] ...................... A61K 39/00; C07K 14/435; C07H 21/00
(52) U.S. Cl. .................... 530/350; 530/358; 424/185.1; 536/23.1; 536/23.5
(58) Field of Search ........................ 424/185.1; 514/12; 530/350, 403; 536/23.1

(56) References Cited

FOREIGN PATENT DOCUMENTS

WO    WO A 92 04472    3/1992

OTHER PUBLICATIONS

Seelig, H.P., et al. The major dermatomyostitis–specific Mi–2 autoantigen is a presumed helicase involved in trascriptional activation. Arthr. Rheum. 38(10)1389–1399, Oct. 1995.*

Wraith, D.C., et al., Antigen recognition in autoimmune encephalomyelitis and the potential for peptide–mediated immunotherapy. Cell. 59:247–255, 1989.*

Tisch, R and McDevitt, H.O. Antigen–specific immunotherapy: is is a real possibility to combat T–cell–mediated autoimmunity? Proc. Natl. Acad. Sci. USA. 91:437–438, Jan. 1994.*

Ngo et al., in The Protein Folding Problem and Tertiary Structure Prediction, 1994, Merz, et al., (ed.), Birkhauser, Boston, MA, pp. 433 and 492–495.*

Mikayama et al, Molecular cloning and functional expression of a cDNA encoding gycosylation–inhibting factor, Nov. 1993, Proc. Natl. Acad. Sci, USA vol. 90: 10056–10060.*

Altschul et al., 1990, "Basic Local Alignment Search Tool," *J. Mol. Biol.* 215:403–410.

Bairoch, A., 1991, "PROSITE: a dictionary of sites and patterns in proteins," *Nucleic Acids Res.* 19:2241.

Frohmann et al., 1988, "Rapid production of full–length cDNAs from rare transcripts: Amplification using a single gene–specific oligonucleotide primer," *Proc. Natl. Acad. Sci. U.S.A.* 85:8998–9002.

Ge et al., 1994, "The Major Antigenic Component of the Mi–2 Autoantigen of Dermatomyositis," *58th National Scientific Meeting of the American College of Rheumatology and the 29th National Scientific Meeting of the Association of Rheumatology Health Professionals, Minneapolis, Minnesota, USA, Oct. 23–27, 1994. Arthritis & Rheumatism* 37:1147.

Ge et al., 1995, "Molecular Analysis of a Major Antigenic Region of the 240–kD Protein of Mi–2 Autoantigen," *J. Clin. Invest.* 96:1730–1737.

Nilasena et al., 1990, "Molecular Cloning of the Dermatomyositis (DM)–Associated Mi–2 Antigen," *54th Annual Meeting of the American College of Rheumatology, Seattle, WA, USA, Oct. 27–Nov. 1, 1990. Arthritis Rheum.* 33(9 Suppl.).

Nilasena et al., 1995, "Analysis of the Mi–2 Autoantigen of Dermatomyositis," *Arthritis & Rheumatism* 38:123–128.

Seelig et al., 1995, "The Major Dermatomyositis Specific Mi–2 Autoantigen is a Presumed Helicase Involved in Transcriptional Activation," *EMBL Datenbank Zugang HSMI2218 Zugriffsnummer*:X86691.

Studier et al., 1990, "Use of T7 RNA Polymerase to Direct Expression of Cloned Genes," *Methods Enzymol.* 185:60–89.

* cited by examiner

*Primary Examiner*—Christina Y. Chan
*Assistant Examiner*—Phuong N. Huynh
(74) *Attorney, Agent, or Firm*—Pennie & Edmonds LLP

(57) ABSTRACT

The present invention relates to a dermatomyositis-specific auto-antigen, a DNA encoding it and a process for the preparation thereof as well as its use.

5 Claims, 16 Drawing Sheets

```
SEQUENCE LISTING

<160> NUMBER OF SEQ ID NOS:  2

<210> SEQ ID NO 1
<211> LENGTH: 6328
<212> TYPE: DNA
<213> ORGANISM: Homo sapiens
<220> FEATURE:
<221> NAME/KEY: CDS
<222> LOCATION: (1)...(5736)

<400> SEQUENCE: 1 atg gcg tcg ggc ctg ggc tcc ccg tcc ccc tgc tcg gcg ggc agt gag      48
Met Ala Ser Gly Leu Gly Ser Pro Ser Pro Cys Ser Ala Gly Ser Glu
1               5                   10                  15 gag gag gat atg gat gca ctt ttg aac aac agc ctg ccc cca ccc cac      96
Glu Glu Asp Met Asp Ala Leu Leu Asn Asn Ser Leu Pro Pro Pro His
            20                  25                  30 cca gaa aat gaa gag gac cca gaa gag gat ttg tca gaa aca gag act     144
Pro Glu Asn Glu Glu Asp Pro Glu Glu Asp Leu Ser Glu Thr Glu Thr
        35                  40                  45 cca aag ctc aag aag aag aaa aag cct aag aaa cct cgg gac cct aaa     192
Pro Lys Leu Lys Lys Lys Lys Pro Lys Lys Pro Arg Asp Pro Lys
    50                  55                  60 atc cct aag agc aag cgc caa aaa aag gag cgt atg ctc tta tgc cgg     240
```

```
Ile Pro Lys Ser Lys Arg Gln Lys Lys Glu Arg Met Leu Leu Cys Arg
 65                  70                  75                  80 cag ctg ggg gac agc tct ggg gag ggg cca gag ttt gtg gag gag gag       288
Gln Leu Gly Asp Ser Ser Gly Glu Gly Pro Glu Phe Val Glu Glu Glu
                     85                  90                  95 gaa gag gtg gct ctg cgc tca gac agt gag ggc agc gac tat act cct       336
Glu Glu Val Ala Leu Arg Ser Asp Ser Glu Gly Ser Asp Tyr Thr Pro
                100                 105                 110 ggc aag aag aag aag aag aag ctt gga cct aag aaa gag aag aag agc       384
Gly Lys Lys Lys Lys Lys Lys Leu Gly Pro Lys Lys Glu Lys Lys Ser
                115                 120                 125 aaa tcc aag cgg aag gag gag gag gag gat gat gat gat gat gat           432
Lys Ser Lys Arg Lys Glu Glu Glu Glu Asp Asp Asp Asp Asp Asp
130                 135                 140 tca aag gag cct aaa tca tct gct cag ctc ctg gaa gac tgg ggc atg       480
Ser Lys Glu Pro Lys Ser Ser Ala Gln Leu Leu Glu Asp Trp Gly Met
145                 150                 155                 160 gaa gac att gac cac gtg ttc tca gag gag gat tat cga acc ctc acc       528
Glu Asp Ile Asp His Val Phe Ser Glu Glu Asp Tyr Arg Thr Leu Thr
                165                 170                 175 aac tac aag gcc ttc agc cag ttt gtc aga ccc ctc att gct gcc aaa       576
Asn Tyr Lys Ala Phe Ser Gln Phe Val Arg Pro Leu Ile Ala Ala Lys
                180                 185                 190 aat ccc aag att gct gtc tcc aag atg atg atg gtt ttg ggt gca aaa       624
Asn Pro Lys Ile Ala Val Ser Lys Met Met Met Val Leu Gly Ala Lys
                195                 200                 205 tgg cgg gag ttc agt acc aat aac ccc ttc aaa ggc agt tct ggg gca       672
Trp Arg Glu Phe Ser Thr Asn Asn Pro Phe Lys Gly Ser Ser Gly Ala
                210                 215                 220 tca gtg gca gct gcg gca gca gcg gta gct gtg gtg gag agc atg           720
Ser Val Ala Ala Ala Ala Ala Val Ala Val Val Glu Ser Met
225                 230                 235                 240 gtg aca gcc act gag gtt gca cca cca cct ccc cct gtg gag gtg cct       768
Val Thr Ala Thr Glu Val Ala Pro Pro Pro Pro Pro Val Glu Val Pro
                245                 250                 255 atc cgc aag gcc aag acc aag gag ggc aaa ggt ccc aat gct cgg agg       816
Ile Arg Lys Ala Lys Thr Lys Glu Gly Lys Gly Pro Asn Ala Arg Arg
                260                 265                 270 aag ccc aag ggc agc cct cgt gta cct gat gcc aag aag cct aaa ccc       864
Lys Pro Lys Gly Ser Pro Arg Val Pro Asp Ala Lys Lys Pro Lys Pro
                275                 280                 285 aag aaa gta gct ccc ctg aaa atc aag ctg gga ggt ttt ggt tcc aag       912
Lys Lys Val Ala Pro Leu Lys Ile Lys Leu Gly Gly Phe Gly Ser Lys
290                 295                 300 cgt aag aga tcc tcg agt gag gat gat gac tta gat gtg gaa tct gac       960
Arg Lys Arg Ser Ser Ser Glu Asp Asp Asp Leu Asp Val Glu Ser Asp
305                 310                 315                 320 ttc gat gat gcc agt atc aat agc tat tct gtt tct gat ggt tcc acc      1008
Phe Asp Asp Ala Ser Ile Asn Ser Tyr Ser Val Ser Asp Gly Ser Thr
                325                 330                 335 agc cgt agt agc cgc agc cgc aag aaa ctc cga acc act aaa aag aaa      1056
Ser Arg Ser Ser Arg Ser Arg Lys Lys Leu Arg Thr Thr Lys Lys Lys
                340                 345                 350 aag aaa ggc gag gag gag gtg act gct gtg gat ggt tat gag aca gac      1104
Lys Lys Gly Glu Glu Glu Val Thr Ala Val Asp Gly Tyr Glu Thr Asp
                355                 360                 365 cac cag gac tat tgc gag gtg tgc cag caa ggc ggt gag atc atc ctg      1152
His Gln Asp Tyr Cys Glu Val Cys Gln Gln Gly Gly Glu Ile Ile Leu
                370                 375                 380
```

```
                                                    -continued tgt gat acc tgt ccc cgt gct tac cac atg gtc tgc ctg gat ccc gac    1200
Cys Asp Thr Cys Pro Arg Ala Tyr His Met Val Cys Leu Asp Pro Asp
385                 390                 395                 400 atg gag aag gct ccc gag ggc aag tgg agc tgc cca cac tgc gag aag    1248
Met Glu Lys Ala Pro Glu Gly Lys Trp Ser Cys Pro His Cys Glu Lys
                405                 410                 415 gaa ggc atc cag tgg gaa gct aaa gag gac aat tcg gag ggt gag gag    1296
Glu Gly Ile Gln Trp Glu Ala Lys Glu Asp Asn Ser Glu Gly Glu Glu
            420                 425                 430 atc ctg gaa gag gtt ggg gga gac ctc gaa gag gag gat gac cac cat    1344
Ile Leu Glu Glu Val Gly Gly Asp Leu Glu Glu Glu Asp Asp His His
        435                 440                 445 atg gaa ttc tgt cgg gtc tgc aag gat ggt ggg gaa ctg ctc tgc tgt    1392
Met Glu Phe Cys Arg Val Cys Lys Asp Gly Gly Glu Leu Leu Cys Cys
450                 455                 460 gat acc tgt cct tct tcc tac cac atc cac tgc ctg aat ccc cca ctt    1440
Asp Thr Cys Pro Ser Ser Tyr His Ile His Cys Leu Asn Pro Pro Leu
465                 470                 475                 480 cca gag atc ccc aac ggt gaa tgg ctc tgt ccc cgt tgt acg tgt cca    1488
Pro Glu Ile Pro Asn Gly Glu Trp Leu Cys Pro Arg Cys Thr Cys Pro
                485                 490                 495 gct ctg aag ggc aaa gtg cag aag atc cta atc tgg aag tgg ggt cag    1536
Ala Leu Lys Gly Lys Val Gln Lys Ile Leu Ile Trp Lys Trp Gly Gln
            500                 505                 510 cca cca tct ccc aca cca gtg cct cgg cct cca gat gct gat ccc aac    1584
Pro Pro Ser Pro Thr Pro Val Pro Arg Pro Pro Asp Ala Asp Pro Asn
        515                 520                 525 acg ccc tcc cca aag ccc ttg gag ggg cgg cca gag cgg cag ttc ttt    1632
Thr Pro Ser Pro Lys Pro Leu Glu Gly Arg Pro Glu Arg Gln Phe Phe
    530                 535                 540 gtg aaa tgg caa ggc atg tct tac tgg cac tgc tcc tgg gtt tct gaa    1680
Val Lys Trp Gln Gly Met Ser Tyr Trp His Cys Ser Trp Val Ser Glu
545                 550                 555                 560 ctg cag ctg gag ctg cac tgt cag gtg atg ttc cga aac tat cag cgg    1728
Leu Gln Leu Glu Leu His Cys Gln Val Met Phe Arg Asn Tyr Gln Arg
                565                 570                 575 aag aat gat atg gat gag cca cct tct ggg gac ttt ggt ggt gat gaa    1776
Lys Asn Asp Met Asp Glu Pro Pro Ser Gly Asp Phe Gly Gly Asp Glu
            580                 585                 590 gag aaa agc cga aag cga aag aac aag gac cct aaa ttt gca gag atg    1824
Glu Lys Ser Arg Lys Arg Lys Asn Lys Asp Pro Lys Phe Ala Glu Met
        595                 600                 605 gag gaa cgc ttc tat cgc tat ggg ata aaa ccc gag tgg atg atg atc    1872
Glu Glu Arg Phe Tyr Arg Tyr Gly Ile Lys Pro Glu Trp Met Met Ile
    610                 615                 620 cac cga atc ctc aac cac agt gtg gac aag aag ggc cac gtc cac tac    1920
His Arg Ile Leu Asn His Ser Val Asp Lys Lys Gly His Val His Tyr
625                 630                 635                 640 ttg atc aag tgg cgg gac tta cct tac gat cag gct tct tgg gag agt    1968
Leu Ile Lys Trp Arg Asp Leu Pro Tyr Asp Gln Ala Ser Trp Glu Ser
                645                 650                 655 gag gat gtg gag atc cag gat tac gac ctg ttc aag cag agc tat tgg    2016
Glu Asp Val Glu Ile Gln Asp Tyr Asp Leu Phe Lys Gln Ser Tyr Trp
            660                 665                 670 aat cac agg gag tta atg agg ggt gag gaa ggc cga cca ggc aag aag    2064
Asn His Arg Glu Leu Met Arg Gly Glu Glu Gly Arg Pro Gly Lys Lys
        675                 680                 685 ctc aag aag gtg aag ctt cgg aag ttg gag agg cct cca gaa acg cca    2112
Leu Lys Lys Val Lys Leu Arg Lys Leu Glu Arg Pro Pro Glu Thr Pro
    690                 695                 700
```

-continued

| | |
|---|---|
| aca gtt gat cca aca gtg aag tat gag cga cag cca gag tac ctg gat<br>Thr Val Asp Pro Thr Val Lys Tyr Glu Arg Gln Pro Glu Tyr Leu Asp<br>705                          710                      715                     720 | 2160 |
| gct aca ggt gga acc ctg cac ccc tat caa atg gag ggc ctg aat tgg<br>Ala Thr Gly Gly Thr Leu His Pro Tyr Gln Met Glu Gly Leu Asn Trp<br>                      725                     730                    735 | 2208 |
| ttg cgc ttc tcc tgg gct cag ggc act gac acc atc ttg gct gat gag<br>Leu Arg Phe Ser Trp Ala Gln Gly Thr Asp Thr Ile Leu Ala Asp Glu<br>                740                     745                    750 | 2256 |
| atg ggc ctt ggg aaa act gta cag aca gca gtc ttc ctg tat tcc ctt<br>Met Gly Leu Gly Lys Thr Val Gln Thr Ala Val Phe Leu Tyr Ser Leu<br>755                      760                    765 | 2304 |
| tac aag gag ggt cat tcc aaa ggc ccc ttc cta gtg agc gcc cct ctt<br>Tyr Lys Glu Gly His Ser Lys Gly Pro Phe Leu Val Ser Ala Pro Leu<br>770                      775                    780 | 2352 |
| tct acc atc atc aac tgg gag cgg gag ttt gaa atg tgg gct cca gac<br>Ser Thr Ile Ile Asn Trp Glu Arg Glu Phe Glu Met Trp Ala Pro Asp<br>785                          790                    795                    800 | 2400 |
| atg tat gtc gta acc tat gtg ggt gac aag gac agc cgt gcc atc atc<br>Met Tyr Val Val Thr Tyr Val Gly Asp Lys Asp Ser Arg Ala Ile Ile<br>                      805                     810                    815 | 2448 |
| cga gag aat gag ttc tcc ttt gaa gac aat gcc att cgt ggt ggc aag<br>Arg Glu Asn Glu Phe Ser Phe Glu Asp Asn Ala Ile Arg Gly Gly Lys<br>                820                     825                    830 | 2496 |
| aag gcc tcc cgc atg aag aaa gag gca tct gtg aaa ttc cat gtg ctg<br>Lys Ala Ser Arg Met Lys Lys Glu Ala Ser Val Lys Phe His Val Leu<br>                      835                     840                    845 | 2544 |
| ctg aca tcc tat gaa ttg atc acc att gac atg gct att ttg ggc tct<br>Leu Thr Ser Tyr Glu Leu Ile Thr Ile Asp Met Ala Ile Leu Gly Ser<br>850                      855                    860 | 2592 |
| att gat tgg gcc tgc ctc atc gtg gat gaa gcc cat cgg ctg aag aac<br>Ile Asp Trp Ala Cys Leu Ile Val Asp Glu Ala His Arg Leu Lys Asn<br>865                          870                    875                    880 | 2640 |
| aat cag tct aag ttc ttc cgg gta ttg aat ggt tac tca ctc cag cac<br>Asn Gln Ser Lys Phe Phe Arg Val Leu Asn Gly Tyr Ser Leu Gln His<br>                      885                     890                    895 | 2688 |
| aag ctg ttg ctg act ggg aca cca tta caa aac aat ctg gaa gag ttg<br>Lys Leu Leu Leu Thr Gly Thr Pro Leu Gln Asn Asn Leu Glu Glu Leu<br>                900                     905                    910 | 2736 |
| ttt cat ctg ctc aac ttt ctc acc ccc gag agg ttc cac aat ttg gaa<br>Phe His Leu Leu Asn Phe Leu Thr Pro Glu Arg Phe His Asn Leu Glu<br>                915                     920                    925 | 2784 |
| ggt ttt ttg gag gag ttt gct gac att gcc aag gag gac cag ata aaa<br>Gly Phe Leu Glu Glu Phe Ala Asp Ile Ala Lys Glu Asp Gln Ile Lys<br>930                      935                     940 | 2832 |
| aaa ctg cat gac atg ctg ggg ccg cac atg ttg cgg cgg ctc aaa gcc<br>Lys Leu His Asp Met Leu Gly Pro His Met Leu Arg Arg Leu Lys Ala<br>945                      950                    955                    960 | 2880 |
| gat gtg ttc aag aac atg ccc tcc aag aca gaa cta att gtg cgt gtg<br>Asp Val Phe Lys Asn Met Pro Ser Lys Thr Glu Leu Ile Val Arg Val<br>                965                     970                    975 | 2928 |
| gag ctg agc cct atg cag aag aaa tac tac aag tac atc ctc act cga<br>Glu Leu Ser Pro Met Gln Lys Lys Tyr Tyr Lys Tyr Ile Leu Thr Arg<br>                980                     985                    990 | 2976 |
| aat ttt gaa gca ctc aat gcc cga ggt ggt ggc aac cag gtg tct ctg<br>Asn Phe Glu Ala Leu Asn Ala Arg Gly Gly Gly Asn Gln Val Ser Leu<br>                995                    1000                  1005 | 3024 |
| ctg aat gtg gtg atg gat ctt aag aag tgc tgc aac cat cca tac ctc<br>Leu Asn Val Val Met Asp Leu Lys Lys Cys Cys Asn His Pro Tyr Leu | 3072 |

-continued

| | | |
|---|---|---|
| 1010 | 1015 | 1020 |

| | | |
|---|---|---|
| ttc cct gtg gct gca atg gaa gct cct aag atg cct aat ggc atg tat | | 3120 |
| Phe Pro Val Ala Ala Met Glu Ala Pro Lys Met Pro Asn Gly Met Tyr | | |
| 1025 1030 1035 1040 | | |

| | | |
|---|---|---|
| gat ggc agt gcc cta atc aga gca tct ggg aaa tta ttg ctg ctg cag | | 3168 |
| Asp Gly Ser Ala Leu Ile Arg Ala Ser Gly Lys Leu Leu Leu Leu Gln | | |
| 1045 1050 1055 | | |

| | | |
|---|---|---|
| aaa atg ctc aag aac ctt aag gag ggt ggg cat cgt gta ctc atc ttt | | 3216 |
| Lys Met Leu Lys Asn Leu Lys Glu Gly Gly His Arg Val Leu Ile Phe | | |
| 1060 1065 1070 | | |

| | | |
|---|---|---|
| tcc cag atg acc aag atg cta gac ctg cta gag gat ttc ttg gaa cat | | 3264 |
| Ser Gln Met Thr Lys Met Leu Asp Leu Leu Glu Asp Phe Leu Glu His | | |
| 1075 1080 1085 | | |

| | | |
|---|---|---|
| gaa ggt tat aaa tac gaa cgc atc gat ggt gga atc act ggg aac atg | | 3312 |
| Glu Gly Tyr Lys Tyr Glu Arg Ile Asp Gly Gly Ile Thr Gly Asn Met | | |
| 1090 1095 1100 | | |

| | | |
|---|---|---|
| cgg caa gag gcc att gac cgc ttc aat gca ccg ggt gct cag cag ttc | | 3360 |
| Arg Gln Glu Ala Ile Asp Arg Phe Asn Ala Pro Gly Ala Gln Gln Phe | | |
| 1105 1110 1115 1120 | | |

| | | |
|---|---|---|
| tgc ttc ttg ctt tcc act cga gct ggg ggc ctt gga atc aat ctg gcc | | 3408 |
| Cys Phe Leu Leu Ser Thr Arg Ala Gly Gly Leu Gly Ile Asn Leu Ala | | |
| 1125 1130 1135 | | |

| | | |
|---|---|---|
| act gct gac aca gtt att atc tat gac tct gac tgg aac ccc cat aat | | 3456 |
| Thr Ala Asp Thr Val Ile Ile Tyr Asp Ser Asp Trp Asn Pro His Asn | | |
| 1140 1145 1150 | | |

| | | |
|---|---|---|
| gac att cag gcc ttt agc aga gct cac cgg att ggg caa aat aaa aag | | 3504 |
| Asp Ile Gln Ala Phe Ser Arg Ala His Arg Ile Gly Gln Asn Lys Lys | | |
| 1155 1160 1165 | | |

| | | |
|---|---|---|
| gta atg atc tac cgg ttt gtg acc cgt gcg tca gtg gag gag cgc atc | | 3552 |
| Val Met Ile Tyr Arg Phe Val Thr Arg Ala Ser Val Glu Glu Arg Ile | | |
| 1170 1175 1180 | | |

| | | |
|---|---|---|
| acg cag gtg gca aag aag aaa atg atg ctg acg cat cta gtg gtg cgg | | 3600 |
| Thr Gln Val Ala Lys Lys Lys Met Met Leu Thr His Leu Val Val Arg | | |
| 1185 1190 1195 1200 | | |

| | | |
|---|---|---|
| cct ggg ctg ggc tcc aag act gga tct atg tcc aaa cag gag ctt gat | | 3648 |
| Pro Gly Leu Gly Ser Lys Thr Gly Ser Met Ser Lys Gln Glu Leu Asp | | |
| 1205 1210 1215 | | |

| | | |
|---|---|---|
| gat atc ctc aaa ttt ggc act gag gaa cta ttc aag gat gaa gcc act | | 3696 |
| Asp Ile Leu Lys Phe Gly Thr Glu Glu Leu Phe Lys Asp Glu Ala Thr | | |
| 1220 1225 1230 | | |

| | | |
|---|---|---|
| gat gga gga gga gac aac aaa gag gga gaa gat agc agt gtt atc cac | | 3744 |
| Asp Gly Gly Gly Asp Asn Lys Glu Gly Glu Asp Ser Ser Val Ile His | | |
| 1235 1240 1245 | | |

| | | |
|---|---|---|
| tac gat gat aag gcc att gaa cgg ctg cta gac cgt aac cag gat gag | | 3792 |
| Tyr Asp Asp Lys Ala Ile Glu Arg Leu Leu Asp Arg Asn Gln Asp Glu | | |
| 1250 1255 1260 | | |

| | | |
|---|---|---|
| act gaa gac aca gaa ttg cag ggc atg aat gaa tat ttg agc tca ttc | | 3840 |
| Thr Glu Asp Thr Glu Leu Gln Gly Met Asn Glu Tyr Leu Ser Ser Phe | | |
| 1265 1270 1275 1280 | | |

| | | |
|---|---|---|
| aaa gtg gcc cag tat gtg gta cgg gaa gaa gaa atg ggg gag gaa gag | | 3888 |
| Lys Val Ala Gln Tyr Val Val Arg Glu Glu Glu Met Gly Glu Glu Glu | | |
| 1285 1290 1295 | | |

| | | |
|---|---|---|
| gag gta gaa cgg gaa atc att aaa cag gaa gaa agt gtg gat cct gac | | 3936 |
| Glu Val Glu Arg Glu Ile Ile Lys Gln Glu Glu Ser Val Asp Pro Asp | | |
| 1300 1305 1310 | | |

| | | |
|---|---|---|
| tac tgg gag aaa ttg ctg cgg cac cat tat gag cag cag caa gaa gat | | 3984 |
| Tyr Trp Glu Lys Leu Leu Arg His His Tyr Glu Gln Gln Gln Glu Asp | | |
| 1315 1320 1325 | | |

| | | |
|---|---|---|
| cta gcc cga aat ctg ggc aaa gga aaa aga atc cgt aaa cag gtc aac | | 4032 |

-continued

```
                Leu Ala Arg Asn Leu Gly Lys Gly Lys Arg Ile Arg Lys Gln Val Asn
                        1330                1335                1340 tac aat gat ggc tcc cag gag gac cga gat tgg cag gac gac cag tcc          4080
Tyr Asn Asp Gly Ser Gln Glu Asp Arg Asp Trp Gln Asp Asp Gln Ser
1345                1350                1355                1360 gac aac cag tcc gat tac tca gtg gct tca gag gaa ggt gat gaa gac          4128
Asp Asn Gln Ser Asp Tyr Ser Val Ala Ser Glu Glu Gly Asp Glu Asp
                1365                1370                1375 ttt gat gaa cgt tca gaa gct ccc cgt agg ccc agt cgt aag ggc ctg          4176
Phe Asp Glu Arg Ser Glu Ala Pro Arg Arg Pro Ser Arg Lys Gly Leu
        1380                1385                1390 cgg aat gat aaa gat aag cca ttg cct cct ctg ttg gcc cgt gtt ggt          4224
Arg Asn Asp Lys Asp Lys Pro Leu Pro Pro Leu Leu Ala Arg Val Gly
            1395                1400                1405 ggg aat att gaa gta ctt ggt ttt aat gct cgt cag cga aaa gcc ttt          4272
Gly Asn Ile Glu Val Leu Gly Phe Asn Ala Arg Gln Arg Lys Ala Phe
        1410                1415                1420 ctt aat gca att atg cga tat ggt atg cca cct cag gat gct ttt act          4320
Leu Asn Ala Ile Met Arg Tyr Gly Met Pro Pro Gln Asp Ala Phe Thr
1425                1430                1435                1440 acc cag tgg ctt gta aga gac ctg cga ggc aaa tca gag aaa gag ttc          4368
Thr Gln Trp Leu Val Arg Asp Leu Arg Gly Lys Ser Glu Lys Glu Phe
                1445                1450                1455 aag gca tat gtc tct ctt ttc atg cgg cat tta tgt gag ccg ggg gca          4416
Lys Ala Tyr Val Ser Leu Phe Met Arg His Leu Cys Glu Pro Gly Ala
            1460                1465                1470 gat ggg gct gag acc ttt gct gat ggt gtc ccc cga gaa ggc ctg tct          4464
Asp Gly Ala Glu Thr Phe Ala Asp Gly Val Pro Arg Glu Gly Leu Ser
        1475                1480                1485 cgc cag cat gtc ctt act aga att ggt gtt atg tct ttg att cgc aag          4512
Arg Gln His Val Leu Thr Arg Ile Gly Val Met Ser Leu Ile Arg Lys
            1490                1495                1500 aag gtt cag gag ttt gaa cat gtt aat ggg cgc tgg agc atg cct gaa          4560
Lys Val Gln Glu Phe Glu His Val Asn Gly Arg Trp Ser Met Pro Glu
1505                1510                1515                1520 ctg gct gag gtg gag gaa aac aag aag atg tcc cag cca ggg tca ccc          4608
Leu Ala Glu Val Glu Glu Asn Lys Lys Met Ser Gln Pro Gly Ser Pro
                1525                1530                1535 tcc cca aaa act cct aca ccc tcc act cca ggg gac acg cag ccc aac          4656
Ser Pro Lys Thr Pro Thr Pro Ser Thr Pro Gly Asp Thr Gln Pro Asn
        1540                1545                1550 act cct gca cct gtc cca cct gct gaa gat ggg ata aaa ata gag gaa          4704
Thr Pro Ala Pro Val Pro Pro Ala Glu Asp Gly Ile Lys Ile Glu Glu
            1555                1560                1565 aat agc ctc aaa gaa gaa gag agc ata gaa gga gaa aag gag gtt aaa          4752
Asn Ser Leu Lys Glu Glu Glu Ser Ile Glu Gly Glu Lys Glu Val Lys
        1570                1575                1580 tct aca gcc cct gag act gcc att gag tgt aca cag gcc cct gcc cct          4800
Ser Thr Ala Pro Glu Thr Ala Ile Glu Cys Thr Gln Ala Pro Ala Pro
1585                1590                1595                1600 gcc tca gag gat gaa aag gtc gtt gtt gaa ccc cct gag gga gag gag          4848
Ala Ser Glu Asp Glu Lys Val Val Val Glu Pro Pro Glu Gly Glu Glu
                1605                1610                1615 aaa gtg gaa aag gca gag gtg aag gag aga aca gag gaa cct atg gag          4896
Lys Val Glu Lys Ala Glu Val Lys Glu Arg Thr Glu Glu Pro Met Glu
        1620                1625                1630 aca gag ccc aaa ggt gct gct gat gta gag aag gtg gag gaa aag tca          4944
Thr Glu Pro Lys Gly Ala Ala Asp Val Glu Lys Val Glu Glu Lys Ser
            1635                1640                1645
```

```
gca ata gat ctg acc cct att gtg gta gaa gac aaa gaa gag aag aaa     4992
Ala Ile Asp Leu Thr Pro Ile Val Val Glu Asp Lys Glu Glu Lys Lys
    1650                1655                1660 gaa gaa gaa gag aaa aaa gag gtg atg ctt cag aat gga gag acc ccc     5040
Glu Glu Glu Glu Lys Lys Glu Val Met Leu Gln Asn Gly Glu Thr Pro
1665                1670                1675                1680 aag gac ctg aat gat gag aaa cag aag aaa aat att aaa caa cgt ttc     5088
Lys Asp Leu Asn Asp Glu Lys Gln Lys Lys Asn Ile Lys Gln Arg Phe
                1685                1690                1695 atg ttt aac att gca gat ggt ggt ttt act gag ttg cac tcc ctt tgg     5136
Met Phe Asn Ile Ala Asp Gly Gly Phe Thr Glu Leu His Ser Leu Trp
            1700                1705                1710 cag aat gaa gag cgg gca gcc aca gtt acc aag aag act tat gag atc     5184
Gln Asn Glu Glu Arg Ala Ala Thr Val Thr Lys Lys Thr Tyr Glu Ile
        1715                1720                1725 tgg cat cga cgg cat gac tac tgg ctg cta gcc ggc att ata aac cat     5232
Trp His Arg Arg His Asp Tyr Trp Leu Leu Ala Gly Ile Ile Asn His
    1730                1735                1740 ggc tat gcc cgg tgg caa gac atc cag aat gac cca cgc tat gcc atc     5280
Gly Tyr Ala Arg Trp Gln Asp Ile Gln Asn Asp Pro Arg Tyr Ala Ile
1745                1750                1755                1760 ctc aat gag cct ttc aag ggt gaa atg aac cgt ggc aat ttc tta gag     5328
Leu Asn Glu Pro Phe Lys Gly Glu Met Asn Arg Gly Asn Phe Leu Glu
                1765                1770                1775 atc aag aat aaa ttt cta gct cga agg ttt aag ctc tta gaa caa gct     5376
Ile Lys Asn Lys Phe Leu Ala Arg Arg Phe Lys Leu Leu Glu Gln Ala
            1780                1785                1790 ctg gtg att gag gaa cag ctg cgc cgg gct gct tac ttg aac atg tca     5424
Leu Val Ile Glu Glu Gln Leu Arg Arg Ala Ala Tyr Leu Asn Met Ser
        1795                1800                1805 gaa gac cct tct cac cct tcc atg gcc ctc aac acc cgc ttt gct gag     5472
Glu Asp Pro Ser His Pro Ser Met Ala Leu Asn Thr Arg Phe Ala Glu
    1810                1815                1820 gtg gag tgt ttg gcg gaa agt cat cag cac ctg tcc aag gag tca atg     5520
Val Glu Cys Leu Ala Glu Ser His Gln His Leu Ser Lys Glu Ser Met
1825                1830                1835                1840 gca gga aac aag cca gcc aat gca gtc ctg cac aaa gtt ctg aaa cag     5568
Ala Gly Asn Lys Pro Ala Asn Ala Val Leu His Lys Val Leu Lys Gln
                1845                1850                1855 ctg gaa gaa ctg ctg agt gac atg aaa gct gat gtg act cga ctc cca     5616
Leu Glu Glu Leu Leu Ser Asp Met Lys Ala Asp Val Thr Arg Leu Pro
            1860                1865                1870 gct acc att gcc cga att ccc cca gtt gct gtg agg tta cag atg tca     5664
Ala Thr Ile Ala Arg Ile Pro Pro Val Ala Val Arg Leu Gln Met Ser
        1875                1880                1885 gag cgt aac att ctc agc cgc ctg gca aac cgg gca ccc gaa cct acc     5712
Glu Arg Asn Ile Leu Ser Arg Leu Ala Asn Arg Ala Pro Glu Pro Thr
    1890                1895                1900 cca cag cag gta gcc cag cag cag tgaagatgca gactgatacc acctccaccg   5766
Pro Gln Gln Val Ala Gln Gln Gln
1905                1910 ctgagcagtg accttcctca ctttctcttg tcccagcttc tcccctgggg gcctgagaga   5826
ccctcacctt cctctgccc atcttccatg ttgtaaagga acagcccag tgcactgggg     5886 gaggggaggg agtgaggggc agtggtgccc ttcctgcaga agagacatgc agcagtagcg   5946
ctggcgccat ctgcaggagc tggcgggctg gccttctgga ccctggcttc tccccactgt   6006
aacgcctgtt acacacaaac tgttgtgggt tcctgccagg cttgaagaaa atgatctgaa   6066
ttttttcctc cttttggttt tattttgttg gtttattttg tgttttcttt tctccttttt   6126
```

-continued

```
gggggggtatt cagagtgggc tgggcccctg ggcgagacac agctacctct gttggcatct    6186
ttttaatacc aggaacccag cggctctagc cactgagcgg ctaaatgaaa taaagtggaa     6246
aaaaaaaaaa aaggaaaaaa ccaaaagcat aaaaaaccac agcaaatttc ttgatgaaaa     6306
ttgaaaataa agtttccttt gt                                              6328
```

<210> SEQ ID NO 2
<211> LENGTH: 1912
<212> TYPE: PRT
<213> ORGANISM: Homo sapiens

<400> SEQUENCE: 2

```
Met Ala Ser Gly Leu Gly Ser Pro Ser Pro Cys Ser Ala Gly Ser Glu
  1               5                  10                  15

Glu Glu Asp Met Asp Ala Leu Leu Asn Asn Ser Leu Pro Pro Pro His
                 20                  25                  30

Pro Glu Asn Glu Glu Asp Pro Glu Glu Asp Leu Ser Glu Thr Glu Thr
             35                  40                  45

Pro Lys Leu Lys Lys Lys Lys Pro Lys Lys Pro Arg Asp Pro Lys
     50                  55                  60

Ile Pro Lys Ser Lys Arg Gln Lys Lys Glu Arg Met Leu Leu Cys Arg
 65                  70                  75                  80

Gln Leu Gly Asp Ser Ser Gly Glu Gly Pro Glu Phe Val Glu Glu Glu
                 85                  90                  95

Glu Glu Val Ala Leu Arg Ser Asp Ser Glu Gly Ser Asp Tyr Thr Pro
                100                 105                 110

Gly Lys Lys Lys Lys Lys Leu Gly Pro Lys Lys Glu Lys Lys Ser
            115                 120                 125

Lys Ser Lys Arg Lys Glu Glu Glu Glu Asp Asp Asp Asp Asp
    130                 135                 140

Ser Lys Glu Pro Lys Ser Ser Ala Gln Leu Leu Glu Asp Trp Gly Met
145                 150                 155                 160

Glu Asp Ile Asp His Val Phe Ser Glu Glu Asp Tyr Arg Thr Leu Thr
                165                 170                 175

Asn Tyr Lys Ala Phe Ser Gln Phe Val Arg Pro Leu Ile Ala Ala Lys
                180                 185                 190

Asn Pro Lys Ile Ala Val Ser Lys Met Met Met Val Leu Gly Ala Lys
            195                 200                 205

Trp Arg Glu Phe Ser Thr Asn Asn Pro Phe Lys Gly Ser Ser Gly Ala
        210                 215                 220

Ser Val Ala Ala Ala Ala Ala Ala Val Ala Val Glu Ser Met
225                 230                 235                 240

Val Thr Ala Thr Glu Val Ala Pro Pro Pro Pro Val Glu Val Pro
                245                 250                 255

Ile Arg Lys Ala Lys Thr Lys Glu Gly Lys Gly Pro Asn Ala Arg Arg
                260                 265                 270

Lys Pro Lys Gly Ser Pro Arg Val Pro Asp Ala Lys Lys Pro Lys Pro
            275                 280                 285

Lys Lys Val Ala Pro Leu Lys Ile Lys Leu Gly Gly Phe Gly Ser Lys
        290                 295                 300

Arg Lys Arg Ser Ser Ser Glu Asp Asp Asp Leu Asp Val Glu Ser Asp
305                 310                 315                 320

Phe Asp Asp Ala Ser Ile Asn Ser Tyr Ser Val Ser Asp Gly Ser Thr
                325                 330                 335
```

```
                    -continued

Ser Arg Ser Ser Arg Ser Arg Lys Lys Leu Arg Thr Thr Lys Lys Lys
                340                 345                 350

Lys Lys Gly Glu Glu Val Thr Ala Val Asp Gly Tyr Glu Thr Asp
            355                 360                 365

His Gln Asp Tyr Cys Glu Val Cys Gln Gln Gly Gly Glu Ile Ile Leu
        370                 375                 380

Cys Asp Thr Cys Pro Arg Ala Tyr His Met Val Cys Leu Asp Pro Asp
385                 390                 395                 400

Met Glu Lys Ala Pro Glu Gly Lys Trp Ser Cys Pro His Cys Glu Lys
                405                 410                 415

Glu Gly Ile Gln Trp Glu Ala Lys Glu Asp Asn Ser Glu Gly Glu Glu
            420                 425                 430

Ile Leu Glu Glu Val Gly Gly Asp Leu Glu Glu Asp Asp His His
        435                 440                 445

Met Glu Phe Cys Arg Val Cys Lys Asp Gly Gly Glu Leu Leu Cys Cys
450                 455                 460

Asp Thr Cys Pro Ser Ser Tyr His Ile His Cys Leu Asn Pro Pro Leu
465                 470                 475                 480

Pro Glu Ile Pro Asn Gly Glu Trp Leu Cys Pro Arg Cys Thr Cys Pro
                485                 490                 495

Ala Leu Lys Gly Lys Val Gln Lys Ile Leu Ile Trp Lys Trp Gly Gln
                500                 505                 510

Pro Pro Ser Pro Thr Pro Val Pro Arg Pro Pro Asp Ala Asp Pro Asn
            515                 520                 525

Thr Pro Ser Pro Lys Pro Leu Glu Gly Arg Pro Glu Arg Gln Phe Phe
            530                 535                 540

Val Lys Trp Gln Gly Met Ser Tyr Trp His Cys Ser Trp Val Ser Glu
545                 550                 555                 560

Leu Gln Leu Glu Leu His Cys Gln Val Met Phe Arg Asn Tyr Gln Arg
                565                 570                 575

Lys Asn Asp Met Asp Glu Pro Pro Ser Gly Asp Phe Gly Gly Asp Glu
            580                 585                 590

Glu Lys Ser Arg Lys Arg Lys Asn Lys Asp Pro Lys Phe Ala Glu Met
            595                 600                 605

Glu Glu Arg Phe Tyr Arg Tyr Gly Ile Lys Pro Glu Trp Met Met Ile
        610                 615                 620

His Arg Ile Leu Asn His Ser Val Asp Lys Gly His Val His Tyr
625                 630                 635                 640

Leu Ile Lys Trp Arg Asp Leu Pro Tyr Asp Gln Ala Ser Trp Glu Ser
                645                 650                 655

Glu Asp Val Glu Ile Gln Asp Tyr Asp Leu Phe Lys Gln Ser Tyr Trp
            660                 665                 670

Asn His Arg Glu Leu Met Arg Gly Glu Glu Gly Arg Pro Gly Lys Lys
        675                 680                 685

Leu Lys Lys Val Lys Leu Arg Lys Leu Glu Arg Pro Pro Glu Thr Pro
            690                 695                 700

Thr Val Asp Pro Thr Val Lys Tyr Glu Arg Gln Pro Glu Tyr Leu Asp
705                 710                 715                 720

Ala Thr Gly Gly Thr Leu His Pro Tyr Gln Met Glu Gly Leu Asn Trp
                725                 730                 735

Leu Arg Phe Ser Trp Ala Gln Gly Thr Asp Thr Ile Leu Ala Asp Glu
            740                 745                 750
```

-continued

```
Met Gly Leu Gly Lys Thr Val Gln Thr Ala Val Phe Leu Tyr Ser Leu
            755                 760                 765

Tyr Lys Glu Gly His Ser Lys Gly Pro Phe Leu Val Ser Ala Pro Leu
        770                 775                 780

Ser Thr Ile Ile Asn Trp Glu Arg Glu Phe Glu Met Trp Ala Pro Asp
785                 790                 795                 800

Met Tyr Val Val Thr Tyr Val Gly Asp Lys Asp Ser Arg Ala Ile Ile
            805                 810                 815

Arg Glu Asn Glu Phe Ser Phe Glu Asp Asn Ala Ile Arg Gly Gly Lys
        820                 825                 830

Lys Ala Ser Arg Met Lys Lys Glu Ala Ser Val Lys Phe His Val Leu
        835                 840                 845

Leu Thr Ser Tyr Glu Leu Ile Thr Ile Asp Met Ala Ile Leu Gly Ser
        850                 855                 860

Ile Asp Trp Ala Cys Leu Ile Val Asp Glu Ala His Arg Leu Lys Asn
865                 870                 875                 880

Asn Gln Ser Lys Phe Phe Arg Val Leu Asn Gly Tyr Ser Leu Gln His
            885                 890                 895

Lys Leu Leu Thr Gly Thr Pro Leu Gln Asn Asn Leu Glu Glu Leu
        900                 905                 910

Phe His Leu Leu Asn Phe Leu Thr Pro Glu Arg Phe His Asn Leu Glu
        915                 920                 925

Gly Phe Leu Glu Glu Phe Ala Asp Ile Ala Lys Glu Asp Gln Ile Lys
        930                 935                 940

Lys Leu His Asp Met Leu Gly Pro His Met Leu Arg Arg Leu Lys Ala
945                 950                 955                 960

Asp Val Phe Lys Asn Met Pro Ser Lys Thr Glu Leu Ile Val Arg Val
            965                 970                 975

Glu Leu Ser Pro Met Gln Lys Lys Tyr Tyr Lys Tyr Ile Leu Thr Arg
            980                 985                 990

Asn Phe Glu Ala Leu Asn Ala Arg Gly Gly Gly Asn Gln Val Ser Leu
            995                 1000                1005

Leu Asn Val Val Met Asp Leu Lys Lys Cys Cys Asn His Pro Tyr Leu
        1010                1015                1020

Phe Pro Val Ala Ala Met Glu Ala Pro Lys Met Pro Asn Gly Met Tyr
1025                1030                1035                1040

Asp Gly Ser Ala Leu Ile Arg Ala Ser Gly Lys Leu Leu Leu Leu Gln
                1045                1050                1055

Lys Met Leu Lys Asn Leu Lys Glu Gly Gly His Arg Val Leu Ile Phe
        1060                1065                1070

Ser Gln Met Thr Lys Met Leu Asp Leu Leu Glu Asp Phe Leu Glu His
        1075                1080                1085

Glu Gly Tyr Lys Tyr Glu Arg Ile Asp Gly Gly Ile Thr Gly Asn Met
        1090                1095                1100

Arg Gln Glu Ala Ile Asp Arg Phe Asn Ala Pro Gly Ala Gln Gln Phe
1105                1110                1115                1120

Cys Phe Leu Leu Ser Thr Arg Ala Gly Gly Leu Gly Ile Asn Leu Ala
                1125                1130                1135

Thr Ala Asp Thr Val Ile Ile Tyr Asp Ser Asp Trp Asn Pro His Asn
            1140                1145                1150

Asp Ile Gln Ala Phe Ser Arg Ala His Arg Ile Gly Gln Asn Lys Lys
        1155                1160                1165

Val Met Ile Tyr Arg Phe Val Thr Arg Ala Ser Val Glu Glu Arg Ile
```

-continued

```
        1170                1175                1180
Thr Gln Val Ala Lys Lys Met Met Leu Thr His Leu Val Val Arg
1185                1190                1195                1200
Pro Gly Leu Gly Ser Lys Thr Gly Ser Met Ser Lys Gln Glu Leu Asp
                1205                1210                1215
Asp Ile Leu Lys Phe Gly Thr Glu Glu Leu Phe Lys Asp Glu Ala Thr
            1220                1225                1230
Asp Gly Gly Gly Asp Asn Lys Glu Gly Glu Asp Ser Val Ile His
            1235                1240                1245
Tyr Asp Asp Lys Ala Ile Glu Arg Leu Leu Asp Arg Asn Gln Asp Glu
            1250                1255                1260
Thr Glu Asp Thr Glu Leu Gln Gly Met Asn Glu Tyr Leu Ser Ser Phe
1265                1270                1275                1280
Lys Val Ala Gln Tyr Val Val Arg Glu Glu Met Gly Glu Glu
                1285                1290                1295
Glu Val Glu Arg Glu Ile Ile Lys Gln Glu Glu Ser Val Asp Pro Asp
                1300                1305                1310
Tyr Trp Glu Lys Leu Leu Arg His His Tyr Gln Gln Gln Glu Asp
            1315                1320                1325
Leu Ala Arg Asn Leu Gly Lys Gly Lys Arg Ile Arg Lys Gln Val Asn
            1330                1335                1340
Tyr Asn Asp Gly Ser Gln Glu Asp Arg Asp Trp Gln Asp Asp Gln Ser
1345                1350                1355                1360
Asp Asn Gln Ser Asp Tyr Ser Val Ala Ser Glu Glu Gly Asp Glu Asp
                1365                1370                1375
Phe Asp Glu Arg Ser Glu Ala Pro Arg Arg Pro Ser Arg Lys Gly Leu
            1380                1385                1390
Arg Asn Asp Lys Asp Lys Pro Leu Pro Pro Leu Leu Ala Arg Val Gly
            1395                1400                1405
Gly Asn Ile Glu Val Leu Gly Phe Asn Ala Arg Gln Arg Lys Ala Phe
        1410                1415                1420
Leu Asn Ala Ile Met Arg Tyr Gly Met Pro Pro Gln Asp Ala Phe Thr
1425                1430                1435                1440
Thr Gln Trp Leu Val Arg Asp Leu Arg Gly Lys Ser Glu Lys Glu Phe
                1445                1450                1455
Lys Ala Tyr Val Ser Leu Phe Met Arg His Leu Cys Glu Pro Gly Ala
                1460                1465                1470
Asp Gly Ala Glu Thr Phe Ala Asp Gly Val Pro Arg Glu Gly Leu Ser
            1475                1480                1485
Arg Gln His Val Leu Thr Arg Ile Gly Val Met Ser Leu Ile Arg Lys
            1490                1495                1500
Lys Val Gln Glu Phe Glu His Val Asn Gly Arg Trp Ser Met Pro Glu
1505                1510                1515                1520
Leu Ala Glu Val Glu Glu Asn Lys Lys Met Ser Gln Pro Gly Ser Pro
                1525                1530                1535
Ser Pro Lys Thr Pro Thr Pro Ser Thr Pro Gly Asp Thr Gln Pro Asn
            1540                1545                1550
Thr Pro Ala Pro Val Pro Pro Ala Glu Asp Gly Ile Lys Ile Glu Glu
            1555                1560                1565
Asn Ser Leu Lys Glu Glu Glu Ser Ile Glu Gly Glu Lys Glu Val Lys
            1570                1575                1580
Ser Thr Ala Pro Glu Thr Ala Ile Glu Cys Thr Gln Ala Pro Ala Pro
1585                1590                1595                1600
```

```
Ala Ser Glu Asp Glu Lys Val Val Glu Pro Pro Glu Gly Glu Glu
            1605                1610                1615

Lys Val Glu Lys Ala Glu Val Lys Glu Arg Thr Glu Glu Pro Met Glu
            1620                1625                1630

Thr Glu Pro Lys Gly Ala Ala Asp Val Glu Lys Val Glu Glu Lys Ser
            1635                1640                1645

Ala Ile Asp Leu Thr Pro Ile Val Glu Asp Lys Glu Glu Lys Lys
        1650                1655                1660

Glu Glu Glu Glu Lys Lys Glu Val Met Leu Gln Asn Gly Glu Thr Pro
1665                1670                1675                1680

Lys Asp Leu Asn Asp Glu Lys Gln Lys Lys Asn Ile Lys Gln Arg Phe
            1685                1690                1695

Met Phe Asn Ile Ala Asp Gly Gly Phe Thr Glu Leu His Ser Leu Trp
            1700                1705                1710

Gln Asn Glu Glu Arg Ala Ala Thr Val Thr Lys Lys Thr Tyr Glu Ile
            1715                1720                1725

Trp His Arg Arg His Asp Tyr Trp Leu Leu Ala Gly Ile Ile Asn His
        1730                1735                1740

Gly Tyr Ala Arg Trp Gln Asp Ile Gln Asn Asp Pro Arg Tyr Ala Ile
1745                1750                1755                1760

Leu Asn Glu Pro Phe Lys Gly Glu Met Asn Arg Gly Asn Phe Leu Glu
            1765                1770                1775

Ile Lys Asn Lys Phe Leu Ala Arg Arg Phe Lys Leu Leu Glu Gln Ala
            1780                1785                1790

Leu Val Ile Glu Glu Gln Leu Arg Arg Ala Ala Tyr Leu Asn Met Ser
            1795                1800                1805

Glu Asp Pro Ser His Pro Ser Met Ala Leu Asn Thr Arg Phe Ala Glu
    1810                1815                1820

Val Glu Cys Leu Ala Glu Ser His Gln His Leu Ser Lys Glu Ser Met
1825                1830                1835                1840

Ala Gly Asn Lys Pro Ala Asn Ala Val Leu His Lys Val Leu Lys Gln
            1845                1850                1855

Leu Glu Glu Leu Leu Ser Asp Met Lys Ala Asp Val Thr Arg Leu Pro
            1860                1865                1870

Ala Thr Ile Ala Arg Ile Pro Pro Val Ala Val Arg Leu Gln Met Ser
        1875                1880                1885

Glu Arg Asn Ile Leu Ser Arg Leu Ala Asn Arg Ala Pro Glu Pro Thr
    1890                1895                1900

Pro Gln Gln Val Ala Gln Gln Gln
1905                1910
```

DERMATOMYOSITIS-SPECIFIC AUTO-ANTIGEN

Figure 1:
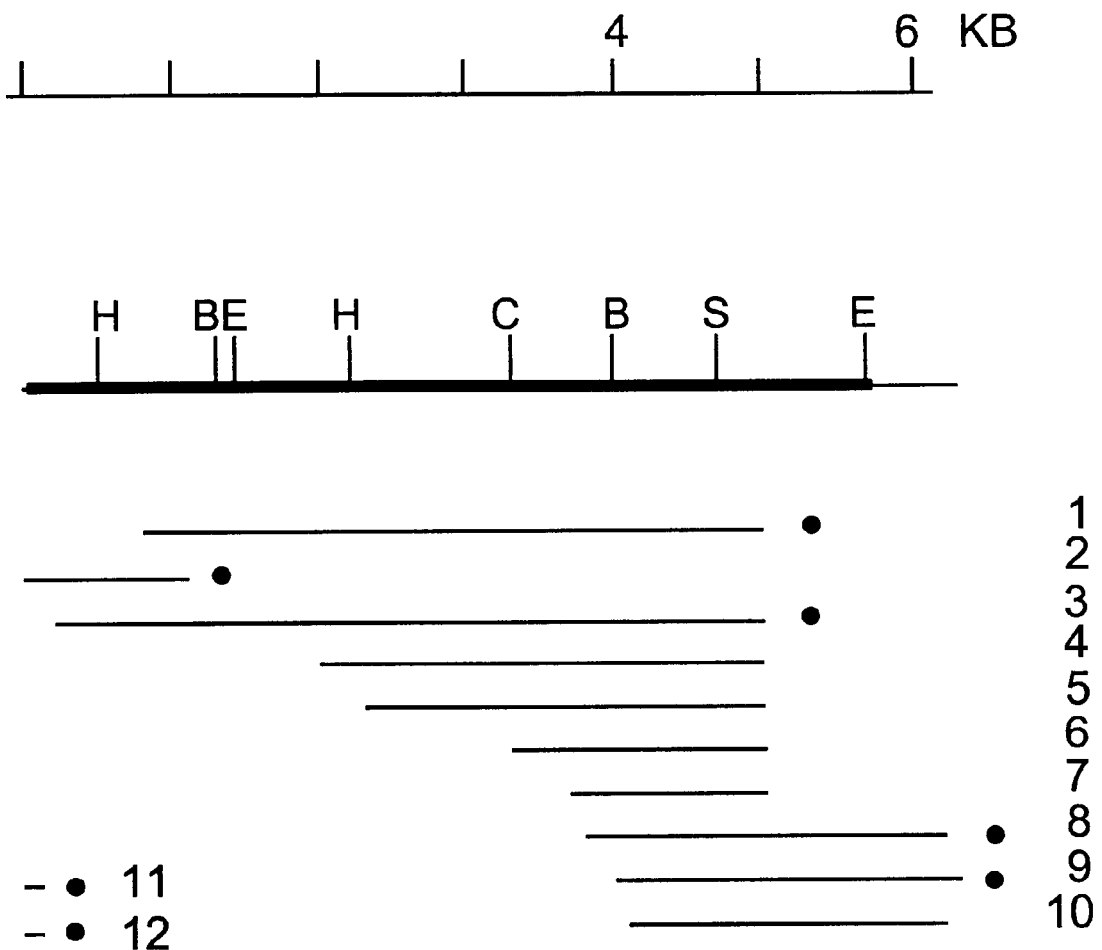

This is a division of application Ser. No. 08/913,832, filed Jan. 12, 1998, now U.S. Pat No. 6,329,517 which is a national phase filing of the Application No. PCT/DE96/00444, which was filed with the Patent Corporation Treaty on Mar. 8, 1996, and is entitled to priority of the German Patent Application 195 09 279.1, filed Mar. 15, 1995.

I. FIELD OF THE INVENTION

The present invention relates to a dermatomyositis-specific auto-antigen, a DNA encoding it and a process for the preparation thereof as well as its use.

II. BACKGROUND OF THE INVENTION

Autoimmune diseases distinguish themselves by the occurrence of autoantibodies, i.e., antibodies directed against constituents of the own organism. Autoantibodies may induce damage of the organism, an organ or part of an organ thus triggering partially serious life-threatening diseases. The origination of such a disease is due to differing pathogenic mechanisms such as neutralization of antigens, e.g., hormones, blocking or stimulation of a receptor for biological active substances, e.g., autoantibodies active against the receptor of the thyroid-stimulating hormone in the case of hyperthyreosis, binding to certain cell or tissue structures accompanied by the induction of a complement-mediated inflammation, e g., glomerulonephritis, antiauto-bodies active against glomerulus basement membranes. Tissues damage may also be induced by cell-mediated mechanisms (autoantibody-dependent cellular cytotoxicity) or by localized and systemic immune complex deposits after the binding of the autoantibodies to soluble antigens.

In addition to such obviously directly damaging autoantibodies, a plurality of autoantibodies active against blood, cell or tissue constituents occur in man, to which a tissue-damaging part cannot be assigned yet clearly by now. The group of rheumatic diseases, particularly the inflammatory rheumatic diseases to which the collagen diseases are attributed, is characterized by the occurrence of numerous autoantibodies. They react, e.g., with antigens of the cell nucleus such as double-stranded DNA, single-stranded DNA, RNA, histones, non-histone proteins, ribonucleoproteins, chromosome-associated antigens, e.g., centromeres or spindle apparatus, or with antigens which are expressed only in certain phases of the cell cycle, e.g., cycline.

The above autoantibodies are found in the case of diseases such as lupus erythematodes, Sjögren's syndrome, mixed connective tissue disease, polymyositis, dermatosclerosis, CREST syndrome, Wegener's granulomatosis and dermatomyositis. They are usually detected by reaction with nuclear extracts from thymocytes of calves or rabbits. Due to this, a differential diagnosis of these diseases, particularly of dermatomyositis, is, however, not possible. But such a diagnosis is a precondition for the selection of treatment.

Therefore, it is the object of the present invention to provide means by which dermatomyositis can be detected by way of differential diagnosis.

III. SUMMARY OF THE INVENTION

The present invention relates to a dermatomyositis-specific auto-antigen, a DNA encoding it and a process for the preparation thereof as well as its use.

IV. BRIEF DESCRIPTION OF THE DRAWINGS

FIG. 1 shows the cloning and composition of the 218 kD Mi-2 cDNA. The upper portion of the illustration shows a restriction map with a scale given in kb. The thick line corresponds to the open reading frame including restriction sites outlined by arrows (H=Hind III; B=BamHI; E=EcoRI; C=ClaI; S=SpHI). The horizontal lines represent isolated clones; the clones sequenced in both mixtures are marked by dots. The two small clones in the lower left-hand corner were obtained according to the RACE protocol. Frohmann et al., 1988, Proc. Natl. Acad Sci. USA. 85:8998–9002). 1: nt 649–4891; 2: nt 0–958; 3: nt 153–4902; 4: nt 1931–4881; 5: nt 2204–4888; 6: nt 3224–4888; 7: nt 3620–4888; 8: nt 3666–6155; 9: nt 3967–6155; 11: nt 178–127; 12: nt 168–127.

Figure 2A:
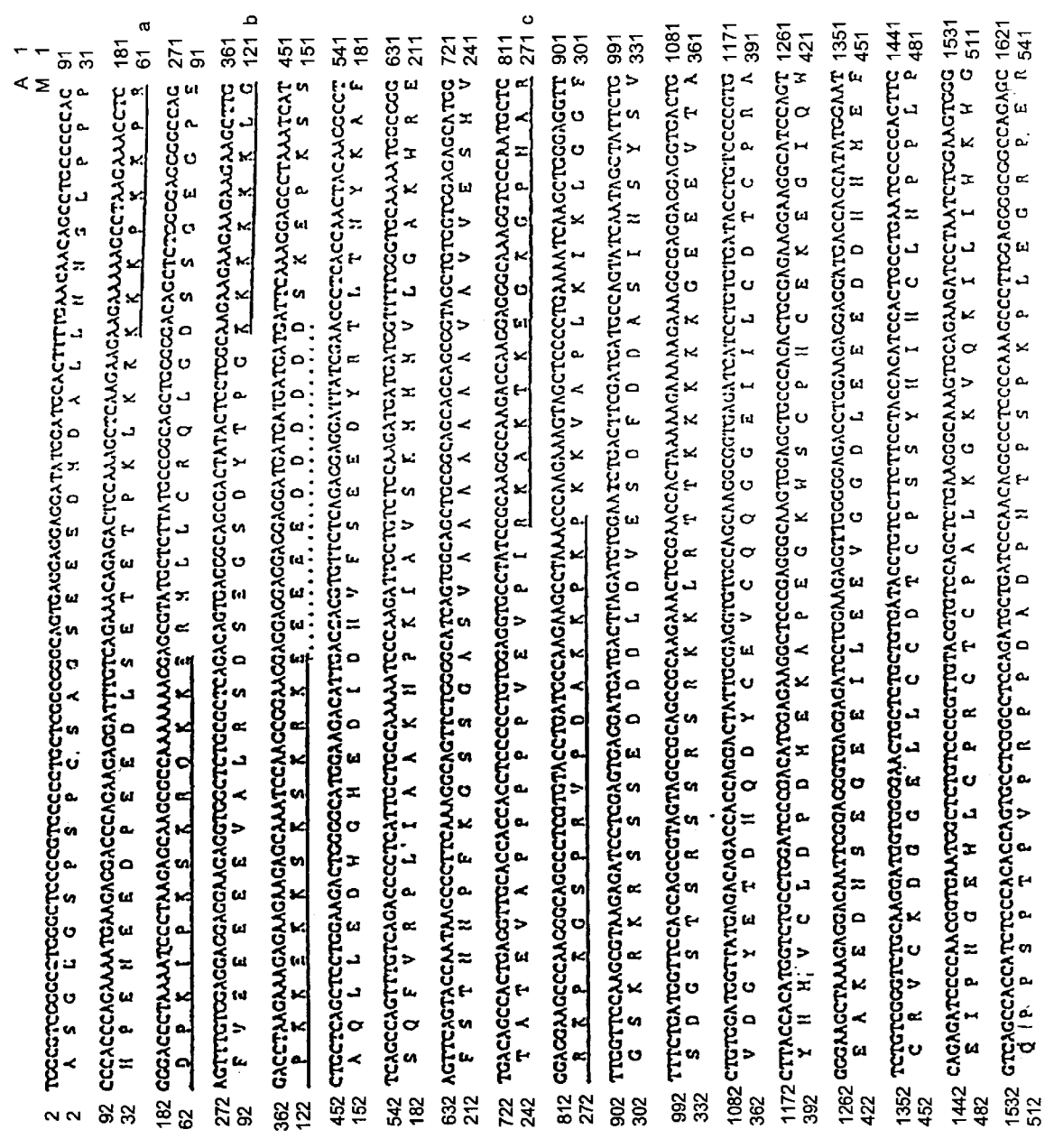
Figure 2B:
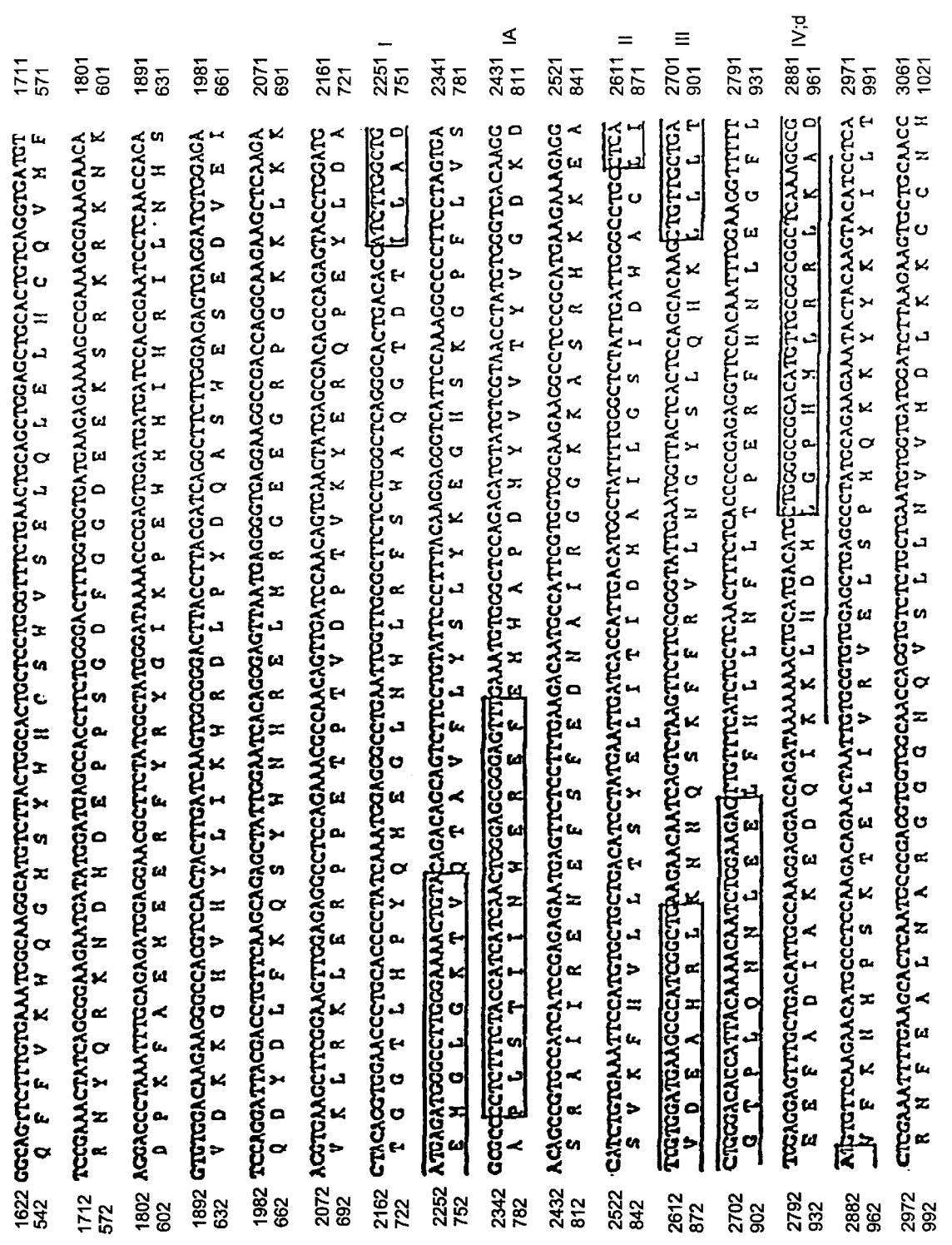
Figure 2C:
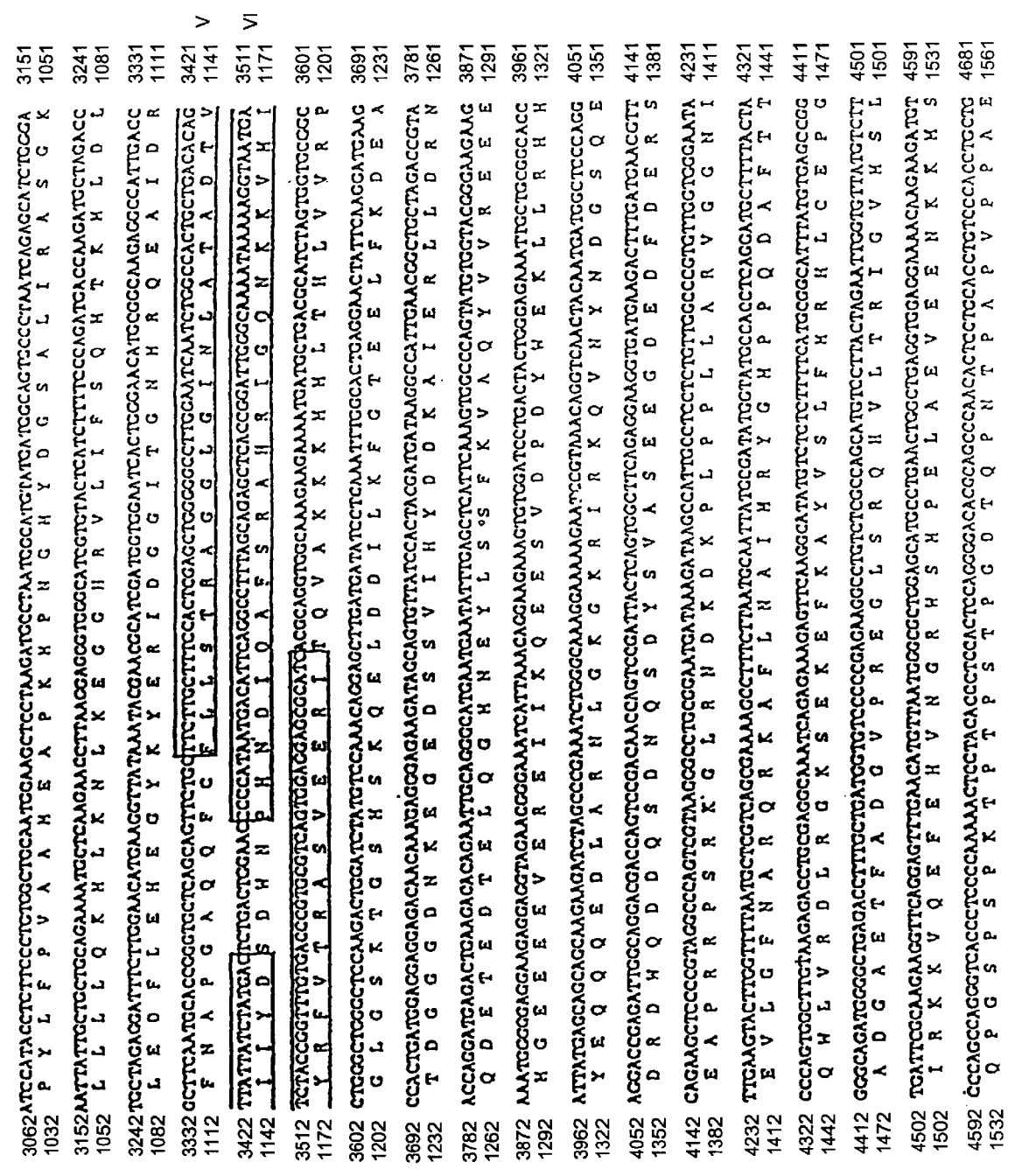
Figure 2D:
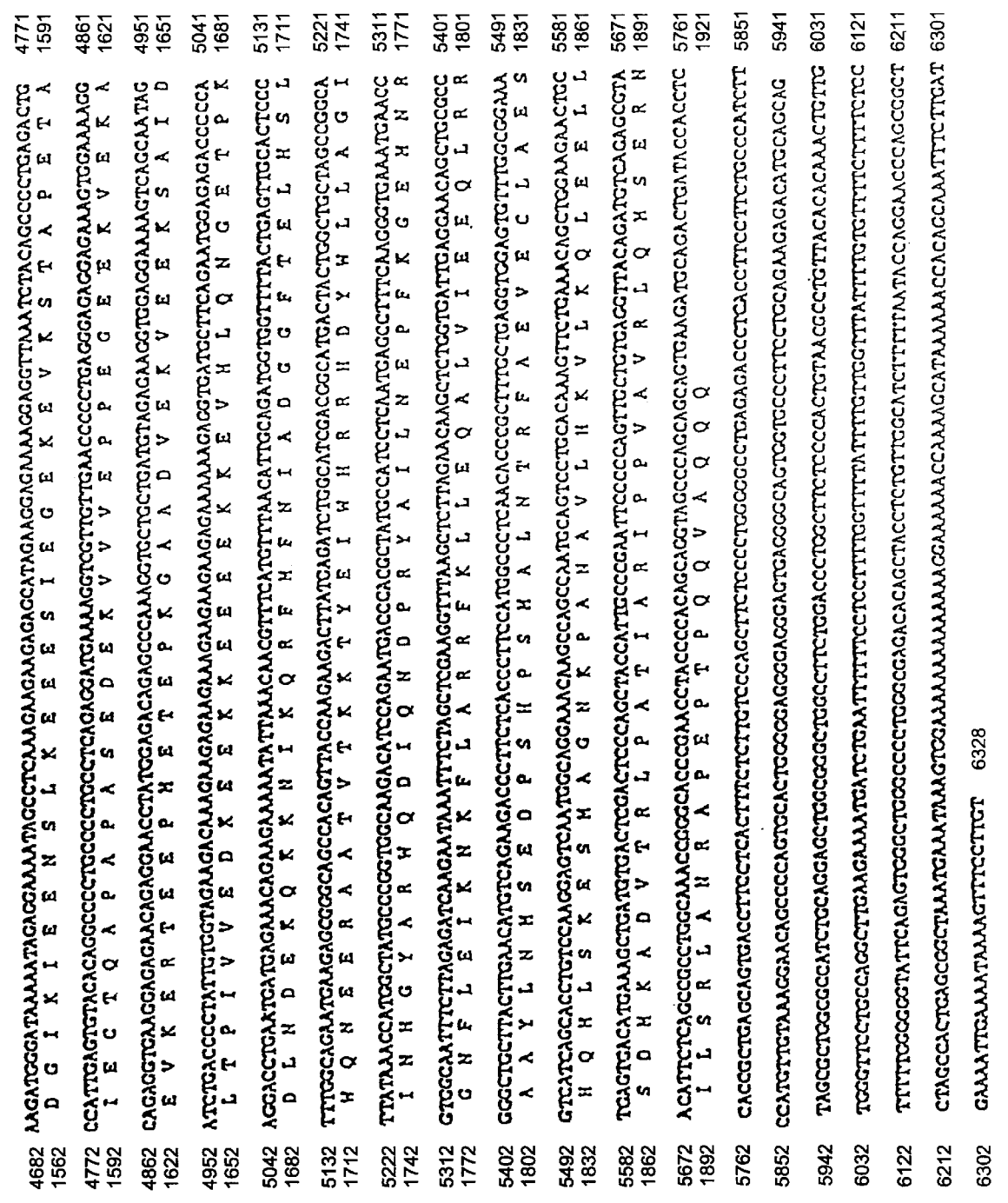

FIGS. 2A–D collectively show the nucleotide sequence (SEQ ID NO: 1) and coding amino acid sequence (SEQ ID NO: 2) of the 218 kD Mi-2 cDNA. The framed sequences show the seven helicase-specific motifs (I, IA, II, III, IV, V and VI). The four underlined regions contain 11 potential nuclear target sequences ten of which are localized in three N-terminal regions (region a contains 3 motifs; region b includes 4 motifs and region C comprises 3 motifs). The dotted line (nt 490–520) shows an accumulation of glutamic acid and asparaginic acid residues which might interact electrostatically with chromatin (histones).

Figure 3:
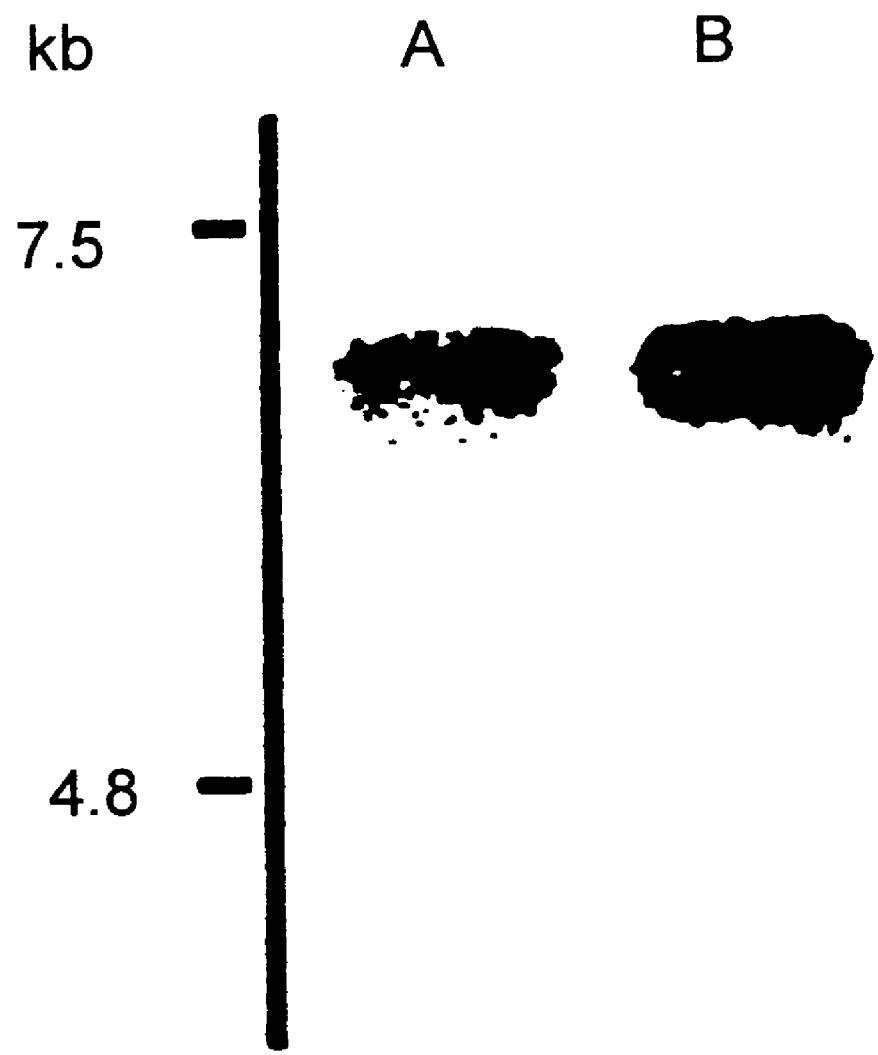

FIG. 3 shows a Northern blot analysis of the 218 kD Mi-2 gene expression in HEp-2 cells. RNA samples were separated in accordance with their size by means of formaldehyde agarose gel electrophoresis and hybridized with $^{32}$P-labeled Mi-2 cDNA subject to a high degree of stringency. Lane A: 5 µg total RNA of HEp-2 cells; lane B: 0.3 µg HEp-2 cells poly(A)⁻ RNA. The size of the bands in the autoradiograph corresponds to about 6.8 kb.

Figure 4:
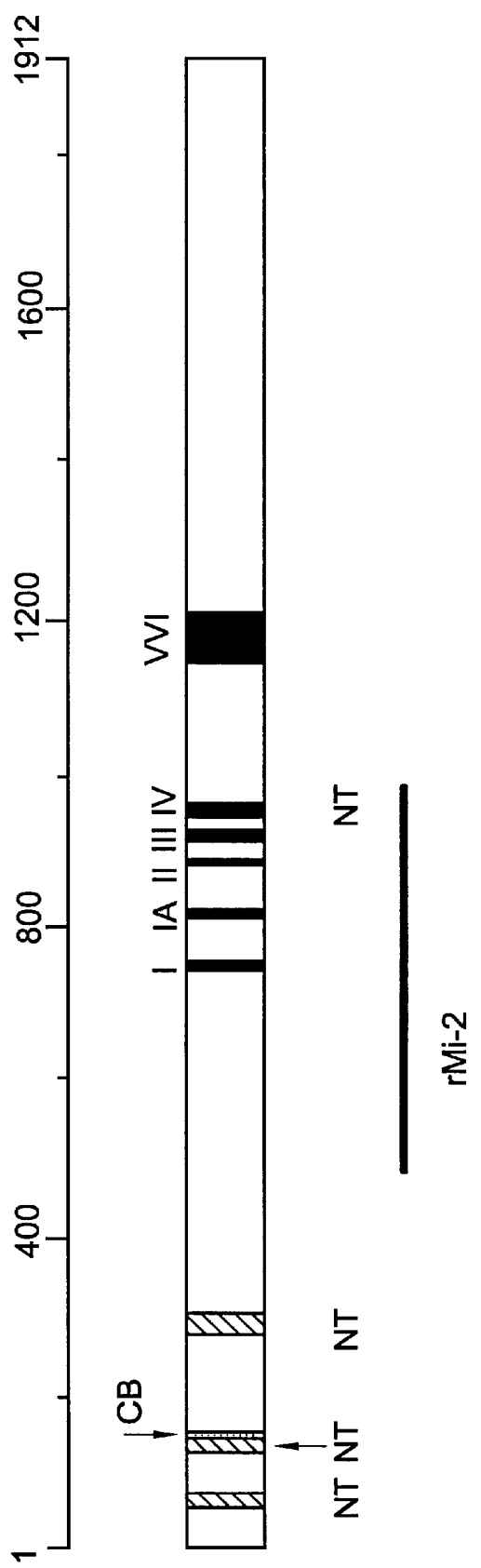

FIG. 4 shows a computer-assisted analysis of functional domains of the 218 kD Mi-2 protein. NT: potential nuclear target sequences; CB: potential chromatin-binding region; I–VI: helicase-specific domains. The thick horizontal line in the lower portion of the illustration shows a recombinant protein (rMi-2) which was used for immunological studies. A scale indicating the positions of the amino acids is plotted on the top.

Figure 5:
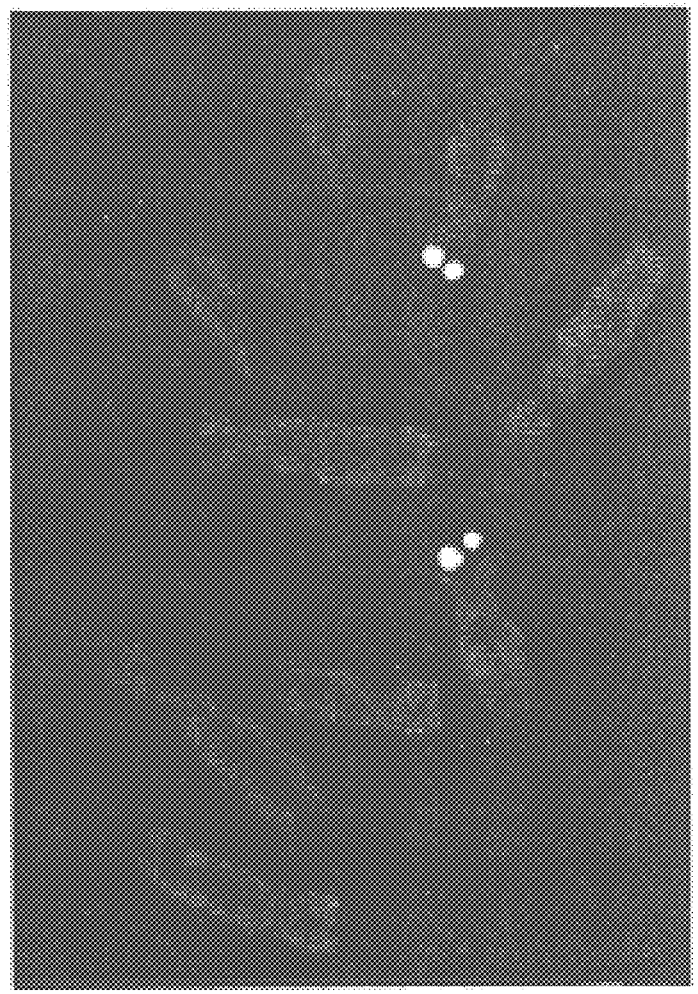

FIG. 5 shows the localization of the 218 kD Mi-2 gene with fluorescence-in situ hybridization (FISH) at the short arm of the human chromosome 12 (12p 13) (arrows).

Figure 6:
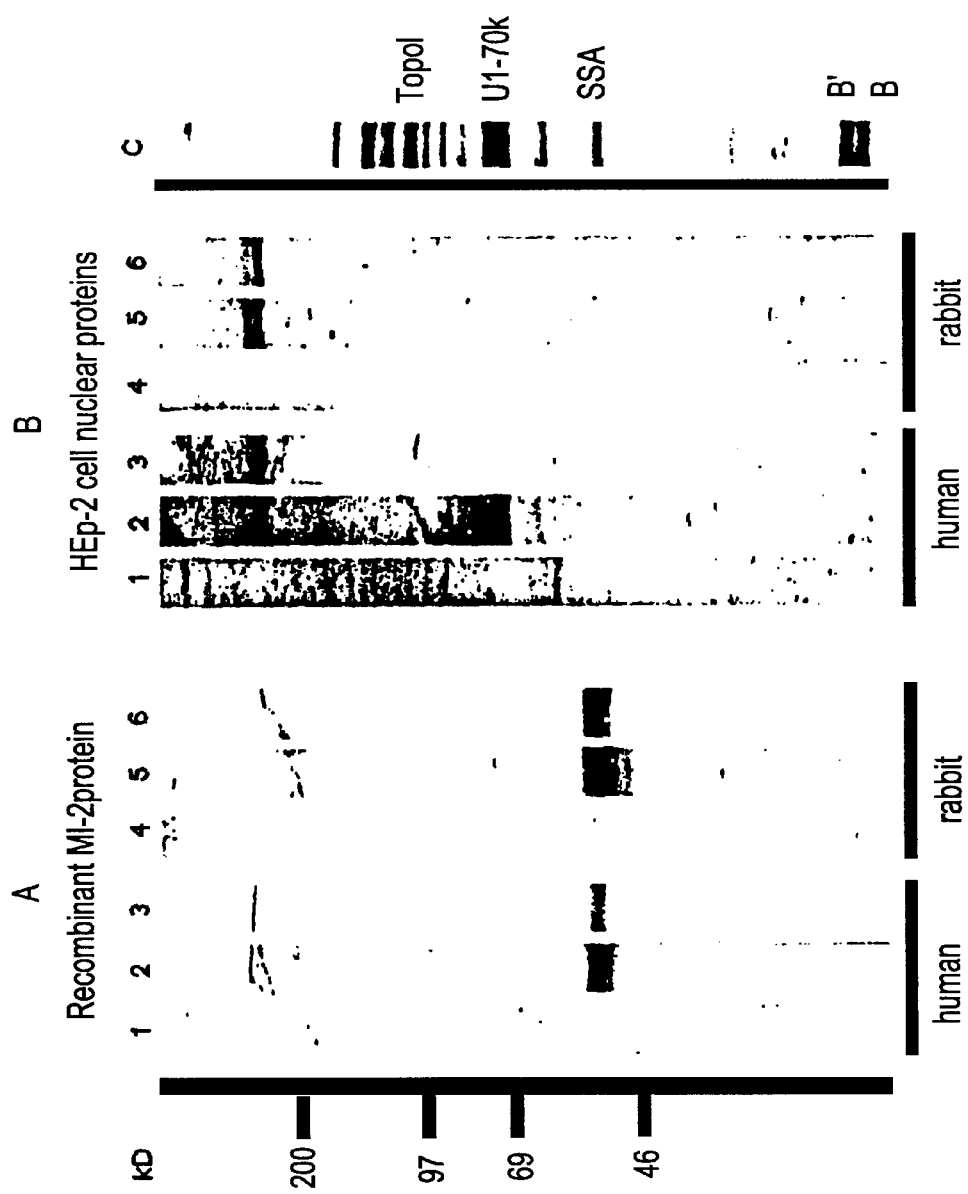

FIG. 6 shows immunoblots of SDS-PAGE-separated (A) recombinant Mi-2 polypeptide (rMi-2) and (B) nuclear proteins of HEp-2 cells which reacted with human sera and rabbit sera and affinity-purified anti-rMi-2-Ig. Lanes A1, B1: human non-reactive control serum. Lanes A2, B2: human anti-Mi-2-positive serum No. 1 (TABLE I) recognizes the rMi-2 with 55 kD (lane A2) as well as the natural 235 kD protein (lane B2) and an additional second natural nuclear protein having 80 kD. Lanes A3, B3: affinity-purified antibodies of serum No. 1 (human anti rMi-2-Ig) react with both the rMi-2 used for affinity purification and the natural 235 kD nuclear protein. The specificity of the antibody preparation is demonstrated in exemplary fashion by the absent reaction with the 80 kD protein. Lane A4, B4: non-reactive rabbit pre-immune serum. Lanes A5 and B5: following immunization with rMi-2, the rabbit serum recognizes the recombinant antigen (rMi-2) and the natural 235 kD protein. Lanes A6 and B6: affinity-purified rabbit antibodies (rabbit anti-rMi-2-Ig) also react with both proteins, the recombinant antigen and the natural 235 kD protein. Lane C (control): core proteins of HEp-2 cells react with a plurality of human antibodies.

Figure 7:
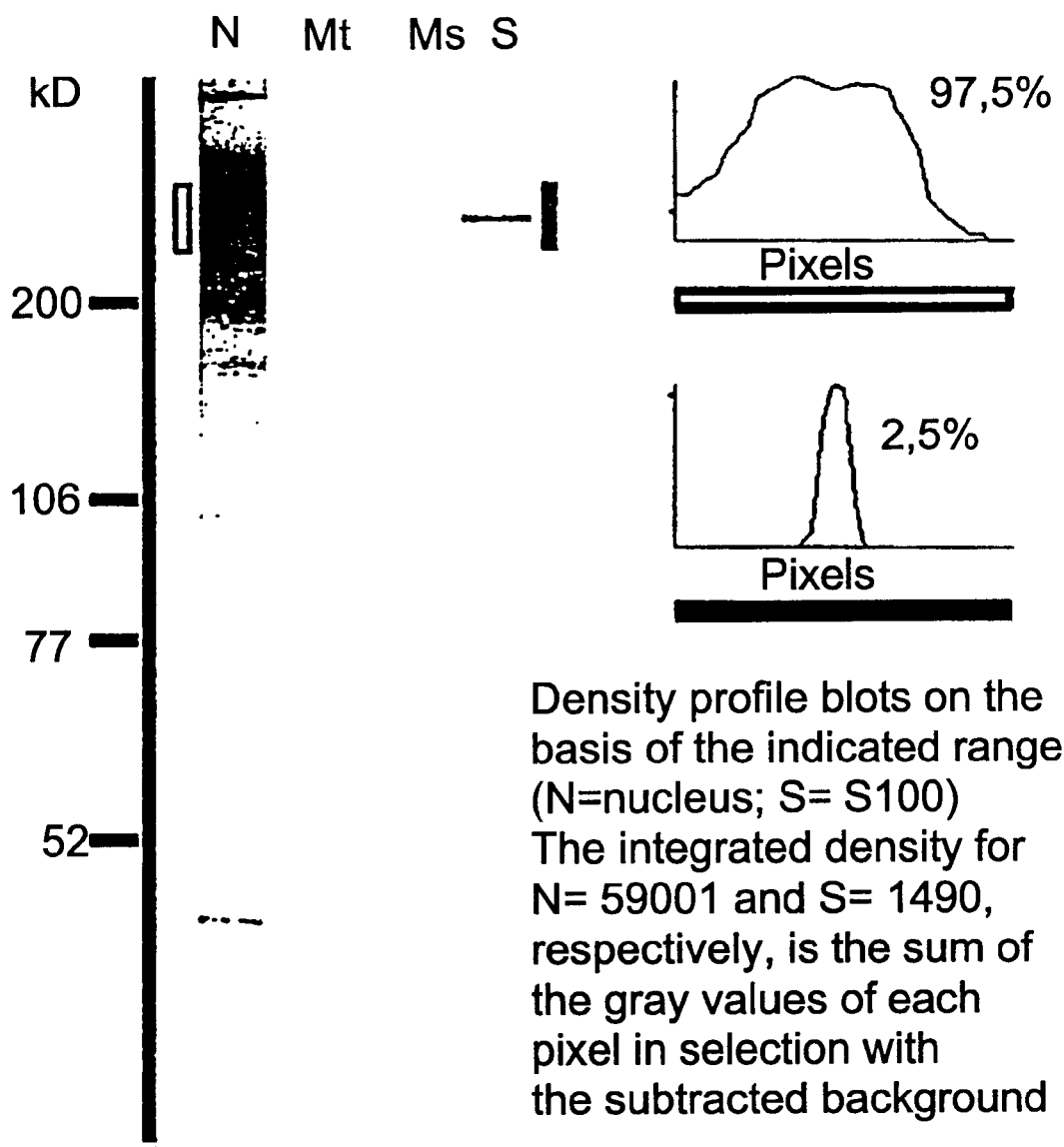

FIG. 7A shows immunoblots of nuclear (N), mitochondrial (Mt), microsomal (Ms) and cytoplasmic (S-100, S) fractions (80 µg protein/cm) of HEp-2 cells which reacted with affinity-purified rabbit-anti-rMi-2 antibodies. The 218 kD Mi-2 protein was found almost exclusively in the nuclear fraction at $M_r$=235 kD. A very small portion of immunoreactive protein can be recognized in the S-100 supernatant. The evaluation of the blot scan yield the following distribution of the 218 kD Mi-2 protein: 97.5% in the nucleus FIG. 7E, 0% each in the mitochondrial and microsomal fractions and 2.5% in the S-100 fraction FIG. 7C.

Figure 8A:
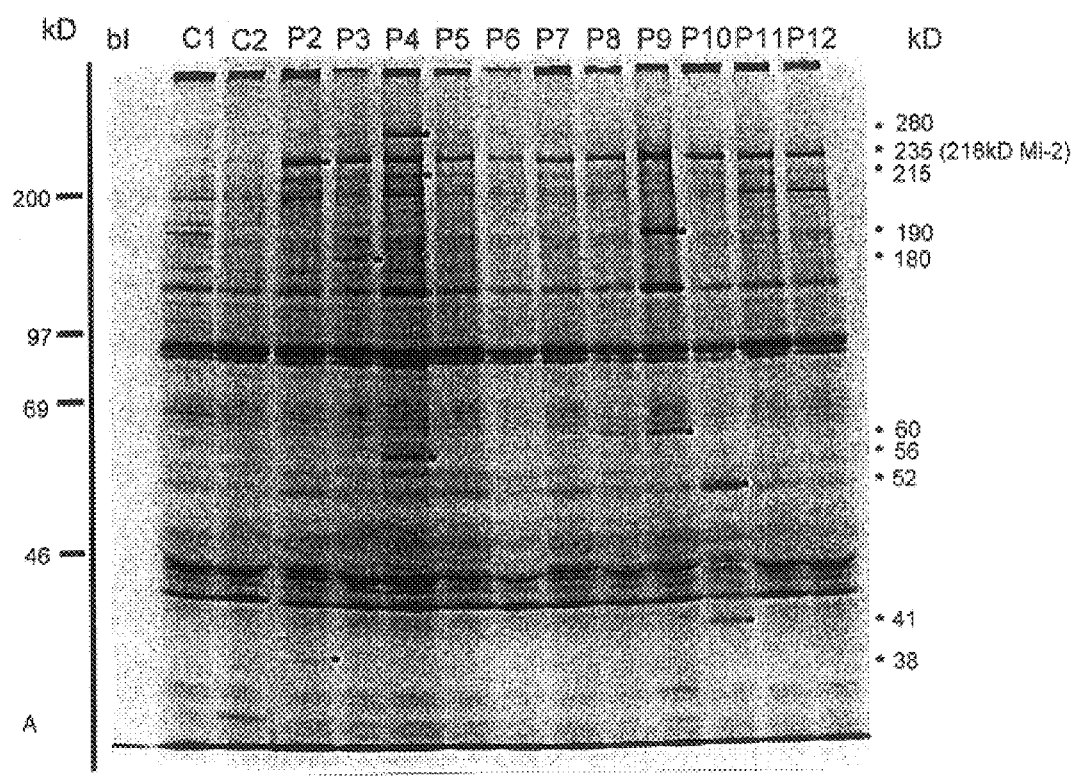

FIG. 8A shows immunoprecipitations of $^{35}$S-methionine-labeled proteins of HEp-2 cell lysates separated by SDS-PAGE with anti-Mi-2 sera (P2-P12) of DM patients and healthy control persons (C1, C2). b1=protein A sepharose alone. All patient sera precipitated a 235 kD protein and furthermore additional proteins which are marked by asterisks on the right-hand side and have individually differing patterns; the molecular weights are indicated additionally.

Figure 8B:
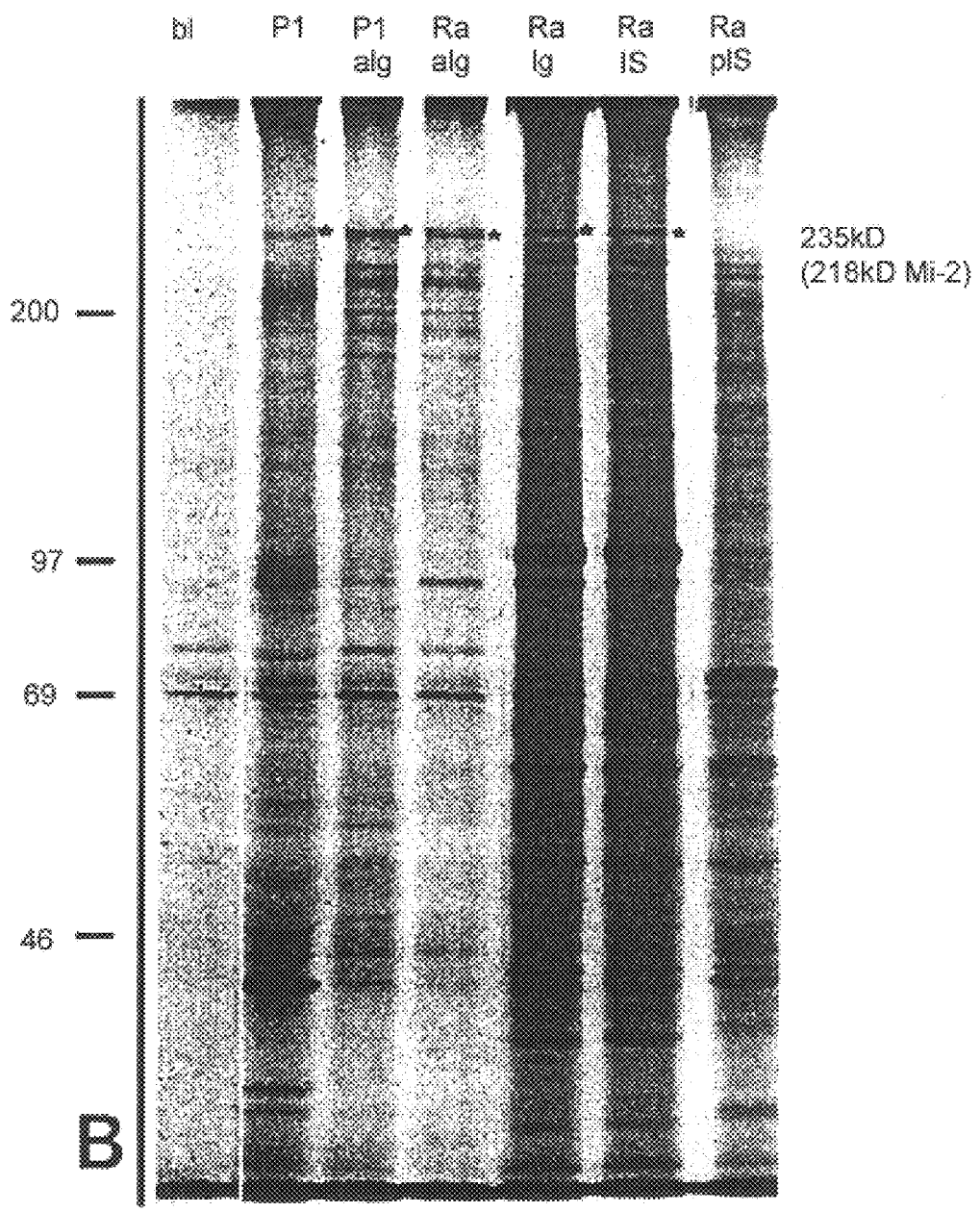

FIG. 8B shows an immunoprecipitation of proteins of a HEp-2 cell lysate with the DM patient serum No. 1 (P1), with rMi-2 protein affinity-purified antibodies of serum No. 1 (P1 alg), affinity-purified rabbit antibodies (Ra alg), rabbit-IgG (Ra Ig), rabbit immune serum (Ra IS) and rabbit pre-immune serum (Ra pIS). Affinity-purified anti-rMi-2 antibodies precipitated the same 235 kD protein as the patient-anti-Mi-2-positive serum.

Figure 8C:
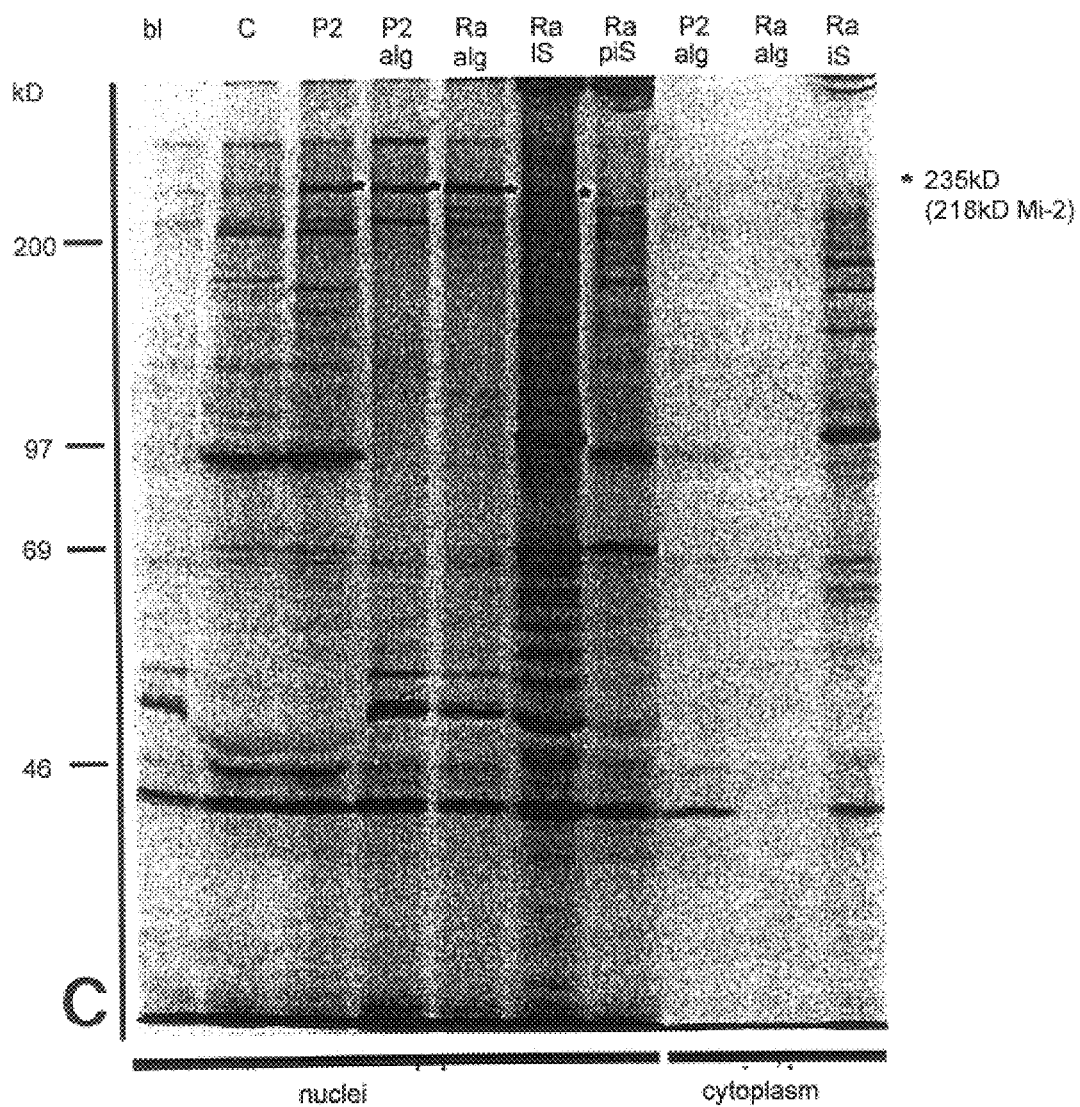

FIG. 8C shows immunoprecipitations of $^{35}$S-methionine-labeled proteins of HEp-2 cell nuclei and cytoplasmic fractions of HEp-2 cells with human serum and rabbit serum. b1=protein A sepharose alone; C=serum of a healthy person; P2=patient No. 2; P2 alg=affinity-purified anti-rMi-2-specific IgG of patient No. 2; Ra alg=affinity-purified anti-rMi-2 Ig of the rabbit; Ra IS=rabbit immune serum; Ra pIS=pre-immune serum. Both the patient serum and the rabbit serum precipitated the 235 kD protein from the nuclear extract but not from cytoplasmic fractions. The patterns obtained with affinity-purified human and rabbit antibodies are almost identical.

Figure 9:
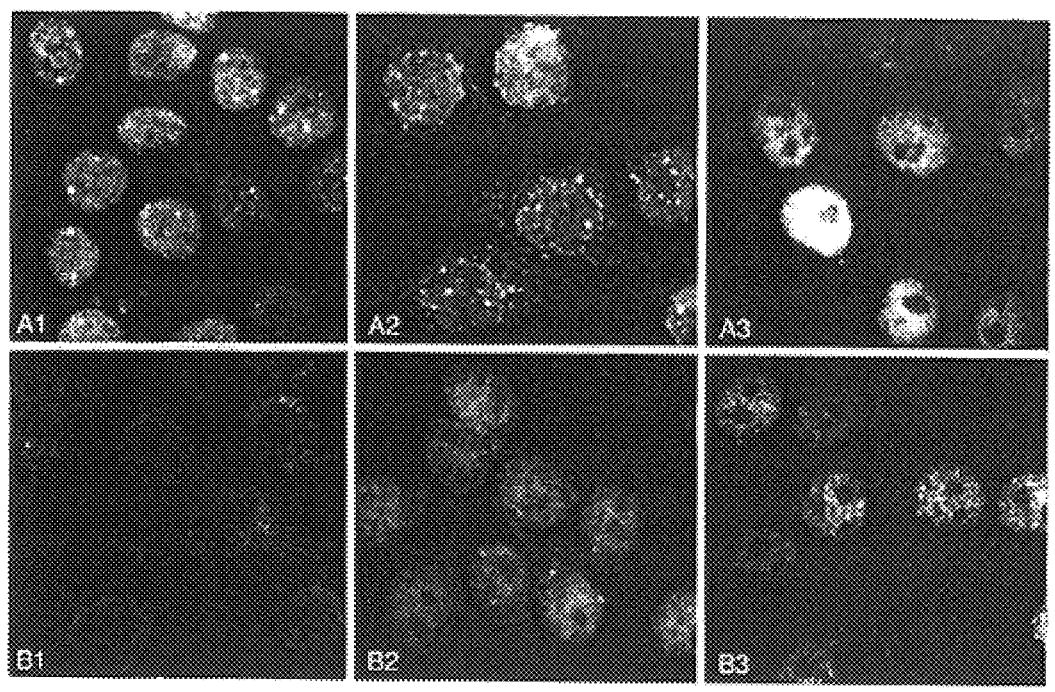

FIG. 9 shows an immunofluorescence of HEp-2 cells with human and rabbit-anti-Mi-2 serum. This immunofluorescence shows a marked nuclear fluorescence. FIG. 9A1: human anti-Mi-2-positive serum (No. 3, TABLE I). FIG. 9A2: serum of patient No. 9, which was admixed with anti-mitochondrial antibodies shows nuclear and mitochondrial fluorescence. FIG. 9A3: the pooled serum shown in FIG. 9A2 was affinity purified with rMi-2, which resulted in an exclusive nuclear fluorescence. FIG. 9B1 rabbit pre-immune serum. FIG. 9B2: a rabbit serum after the second booster with rMi-2 antigen showed intense nuclear fluorescence. FIG. 9B3: the affinity-purified rabbit-anti-M2 antibodies dyed the nucleus.

Figure 10:
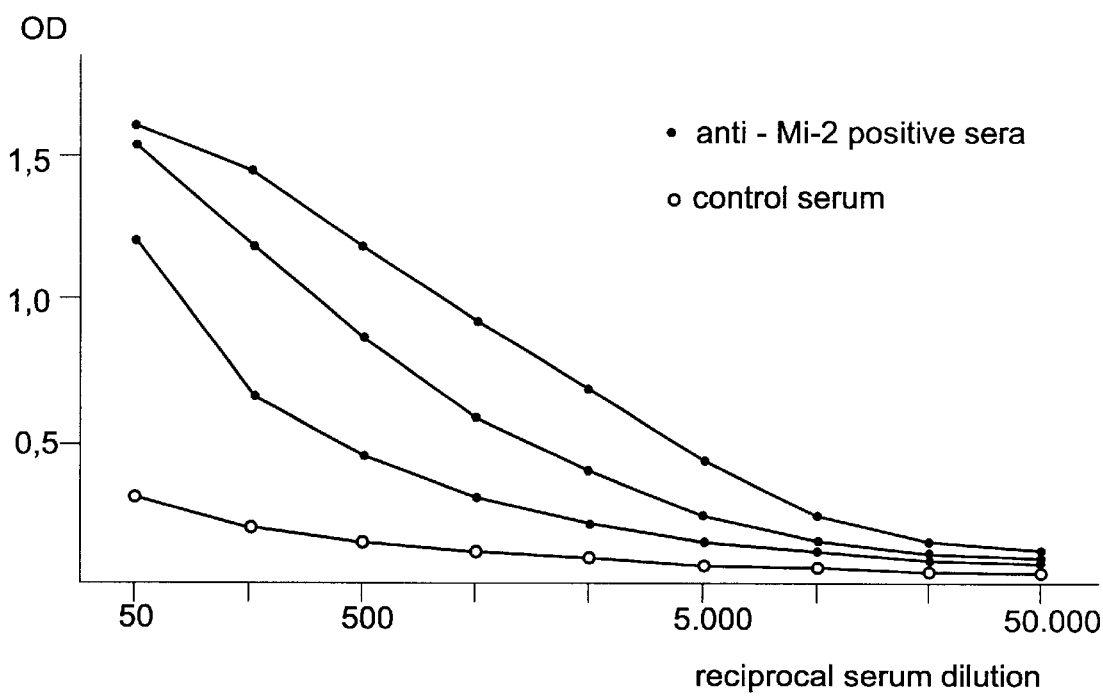

FIG. 10 shows an ELISA with rMi-2 antigen for the detection of anti-218 kD Mi-2 antibodies. Recesses of microtiter plates were coated with 0.8 µg rMi-2 antigen and blocked with BSA. ODs of series dilutions of anti-Mi-2-positive sera and a control serum are shown. For testing human sera, dilutions of 1:200 were chosen.

Figure 11:
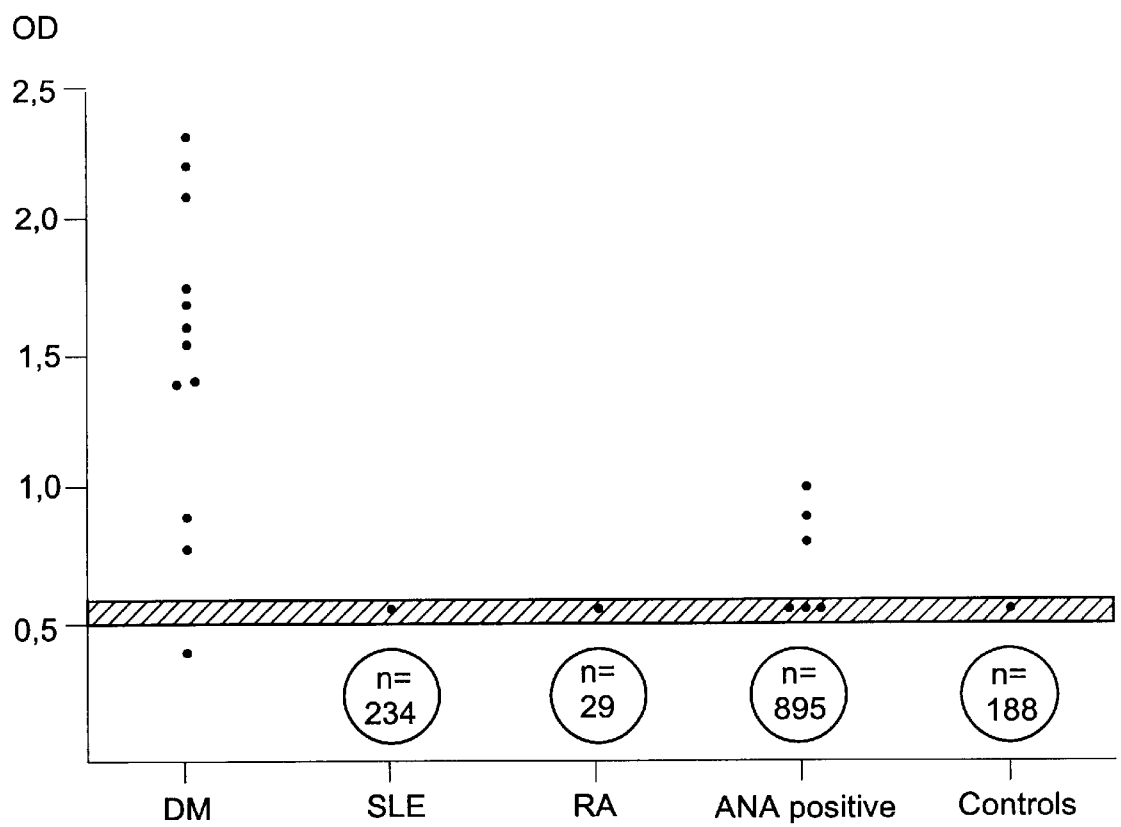

FIG. 11 shows the detection of anti-Mi-2 antibodies with the recombinant protein-ELISA. Dashed line: border region (OD 0.5–0.6). The encircled numbers designate the number of tested negative sera having ODs between 0.05 and 0.5. DM: dermatomyositis; SLE: systemic lupus erythematodes; RA: rheumatoid arthritis; ANA positive sera: sera which were submitted for the analysis for ANA and reacted positively with HEp-2 cells (titer 1: ≧160). Controls: sera of healthy persons.

V. DETAILED DESCRIPTION OF THE INVENTION

It is one the object of the present invention to provide means by which dermatomyositis can be detected by way of differential diagnosis.

According to the invention, this is achieved by providing the subject matters in the claims.

Thus, the subject matter of the invention relates to a dermatomyositis-specific auto-antigen which comprises the amino acid sequence of FIGS. 2A–D or a functional derivative or fragment thereof.

The expression "functional derivative or fragment" comprises any derivative or fragment of the amino acid sequence of FIGS. 2A–D against which an autoantibody can be formed. In particular, the expression relates to epitopes in the amino acid sequence which may act as antigens. Also, it is self-evident that the amino acid sequence of FIGS. 2A–D may include additions, substitutions and/or deletions of one or more amino acids, which also applies to the functional derivatives or fragments thereof.

Another subject matter of the invention relates to a nucleic acid coding for an above auto-antigen. This may be an RNA or a DNA. The latter can be e.g., a genomic DNA or a cDNA. Preferred is a DNA which comprises the following:

(a) the DNA of FIGS. 2A–D or a portion thereof, (b) a DNA hybridizing with the DNA of (a), or (c) a DNA related to the DNA of (a) or (b) via the degenerated genetic code.

The expression of "hybridizing DNA" refers to a DNA which hybridizes under conventional conditions, particularly 20° C. below the DNA melting point, with a DNA of (a).

The DNA of FIGS. 2A–D was deposited as *E. coli* Hi-FI-213 under DSM 9800 with the DSM [German-type collection of microorganisms, Mascheroder Weg 1b, D-38124 Braunschweig, Germany,] on Mar. 13, 1995.

A DNA according to the invention and an auto-antigen coded by it are referred to below as "Mi-2 DNA" ("Mi-2 cDNA") and "Mi-2 antigen", respectively. This is due to the fact that for the production of such a DNA sera from dermatomyositis patients can be used, which are referred to as "anti-Mi-2 positive". In this connection, "Mi-2" refers to the patient's serum which reacted for the first time with the nuclear extracts from thymocytes of calves or rabbits.

For the preparation of an Mi-2 cDNA it is favorable to screen a lambda phage expression library with the above patient sera. Positive clones may then be sequenced and optionally be used for further screening. The inventive preparation of an Mi-2 cDNA is described in Examples 1 to 2. Its structural elucidation as well as that of the Mi-2 antigen coded by it are described in Examples 3 to 5.

According to the invention of an Mi-2 cDNA may be present in a vector and expression vector, respectively. A person skilled in the art is familiar with examples thereof. In the case of an expression vector for *E. coli*, these are, e.g., pGEMEX, pUC derivatives, pGEX-2T and pET3b, the latter being preferred. For the expression in yeast e.g., pY100 and Ycpad1 have to be mentioned while for the expression in animal cells e.g., pKCR, pEFBOS, cDM8 and pCEV4 have to be indicated.

The person skilled in the art is familiar with cells suitable to express an Mi-2 cDNA present in an expression vector. Examples of such cells comprise the *E. coli* strains HB101, DH1, x1776, JM101, JM109 and BL21, the latter being preferred, the yeast strain *Saccharomyces cerevisiae* and the animal cells L, 3T3, FM3A, CHO, COS, Vero and HeLa.

The person skilled in the art knows in which way an Mi-2 cDNA has to be inserted in an expression vector. He is also familiar with the fact that this DNA can be inserted in combination with a DNA coding for another protein and peptide, respectively, so that the Mi-2 cDNA can be expressed in the form of a fusion protein.

Furthermore, the person skilled in the art knows conditions of cultivating transformed cells and transfected cells, respectively. He is also familiar with processes of isolating and purifying the expressed Mi-2 antigen. Thus, an above, recombinantly prepared Mi-2 antigen (referred to below as rMi-2 antigen) which may also be a fusion protein, also belongs to the subject matter of the invention.

Auto-antigens according to the invention distinguish themselves in that they recognize dermatomyositis-specific autoantibodies. Therefore, they are suited for the differential diagnosis of collagen diseases, particularly of dermatomyositis. Such a diagnosis can be made by common detection methods, particularly a Western blot, an ELISA, an immunoprecipitation or an immunofluorescence. For this purpose, the auto-antigens according to the invention may be labeled, if appropriate, or be used in combination with labeled antibodies directed thereagainst.

Furthermore, auto-antigens according to the invention may be present in a kit. It may contain the auto-antigens, as indicated in the above form, together with conventional additives such as buffers and carrier material. Such a kit also belongs to the subject matter of the invention.

Furthermore, the auto-antigens according to the invention are also suited for therapeutic purposes. For example, they can serve for removing autoantibodies from the circulation of dermatomyositis patients by way of affinity chromatography. One should also have in mind a removal of dermatomyositis-specific autoantibody-producing lymphocytes by linkage of the auto-antigens according to the invention to cell toxins.

Besides, nucleic acids according to the invention, particularly DNAs, are suitable for all kinds of diagnostic purpose.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed. various modifications of the invention in addition to those described herein will become apparent to those skilled in the art from the foregoing description and accompanying drawings. Such modifications are intended to fall within the scope of the appended claims.

VI. EXAMPLES

A. Example 1

Screening and Isolation of Recombinant Lambda Phages

The IgG fraction of a human anti-Mi-2-positive serum was isolated by DEAE SEPHAROSE™ chromatography and used for screening about 400 000 plagues of an oligo (dT)-primed HeLa cDNA expression library (λ UNIZAPXR™, Stratagene, Heidelberg). Following repeated purification, a positive clone was obtained and sequenced. Two 40-*meric* oligonucleotides which were complementary to the two ends of the insert of this clone (4.3 kb) were used after radioactive labeling for re-screening of the same library to obtain further cDNAs in the 5' and 3' directions. Furthermore, even shorter 5' clones were additionally obtained by an AMPLIFINDER™ RACE kit (Clontech, Palo Alto, Calif., U.S.A.) and cloning into the plasmid-BLUESCRIPT KS™ (Stratagene). A total of 15 clones were isolated.

B. Example 2

Sequencing of the Clones and Structure of the Entire Mi-2 cDNA

Bluescript KS plasmids were excised from the λ-clones by means of helper phages according to the manufacturer's instructions (Stratagene) and the DNAs were sequenced following characterization by hybridization and purification using Quiagen columns (available from Quiagen GmbH, Düsseldorf) by means of a sequencing machine (ALF™, Pharmacia, Freiburg) according to the dideoxy method using fluorescence ATP (Boehringer Mannheim). All sequences of the clones were prepared according to a walking primer strategy, the clones having bee sequenced in both directions. The sequence data was combined by means of the ASSEMGEL™ Software of PC-GEne (IntelliGenetics Inc., Brussels, Belgium).

C. Example 3

Nucleotide Sequence and Derived Amino Acid Sequence of the Mi-2 cDNA

Computer-assisted sequence analyses were carried out by means of the GCG Software (Genetics Computer Group, Madison, Wis., U.S.A.). The EMBL nucleic acid and the SWISS-PROT protein sequence data banks were scanned with the BLASTN and BLASTP algorithms (Altschul et al., 1990, *J. Mol. Biol.* 215:403–410) as to the presence of local similarities with individual sequences in the Mi-2 nucleic acid/amino acid sequence. The search for functional motifs was carried out with the PROSITE algorithm. Bairoch, 1991, *Nucleic Acids Res.* 19:2241–2245, Supplement. The cloning and sequencing strategy yielded the nucleic acid sequence shown in FIGS. 2A–D and the amino acid sequence derived therefrom. The first ATG (nt 1) is located in an environment which is favored for translocation initiation and starts an open reading frame of 5736 bp which codes for a protein having 1912 amino acids (217989 Dalton) (218 kD Mi-2 protein).

A sequence motif (AAATAAA) very similar to the polyadenylation-consensus signal (AATAAA) is found in the non-translated 3' region of nt 6143–6151. The 218 kD Mi-2 antigen is a hydrophilic acidic protein (p1=5.48) having almost uniform distribution of charged or polar and hydrophobic amino acids which are embedded in N-glycosylation and N-myrostoylation motifs. Furthermore, there are many potential phosphorylation sites.

The search for sequence similarities between the 218 kD Mi-2 antigen and other proteins did not yield any marked homology with respect to the sequences deposited it the data banks. However, several functional domains in the 218 kD Mi-2 protein could be identified clearly. The most prominent regions are characteristic of helicases and are located in the central portion of the protein. The most striking similarities waqs shown by 20 proteins all of which belong to a superfamily of helicases, defined by the SNF2 and RAD54 yeast helicases. Bairoch, 1991, supra.

D. Example 4

Size of the Mi-2 mRNA

Total RNA and poly (A)+ RNA were isolated from a human cell line, separated electrophoretically in a formaldehyde agarose gel according to their sizes and hybridized with radioactively labeled Mi-2 cDNA after transfer to a membrane. The autoradiograph (FIG. 3) shows a signal at about 6.8 kb. This experiment demonstrates that the Mi-2 mRNA is long enough to comprise the 5.7 kb long Mi-2 cDNA.

E. Example 5

Chromosomal Localization of the 218 kiD Mi-2 Gene

A fragment of the Mi-2 cDNA (nt 153–4902) was labeled with biotin-dUTP and used for in situ hybridization of human metaphase chromosomes. Hybridized DNA was detected with a fluorescein isothiocyanate-labeled avidin (Jackson Immuno. Research Laboratories, West Grove, Pa., U.S.A.) and an axiophot photomicroscope (Zeiss, Oberkochen). Pictures were digitized with a CCD camera (Photometrics, Tuscon, Ariz., U.S.A) and processed with an Apple computer system. Specific fluorescence signals were observed on the distal side of the short arm of chromosome 12 (12p 13). Twelve of eighteen investigated metaphase chromosomes showed specific signals at both homologues).

F. Example 6

Synthesis of Part of the Coding Region of the Mi-2 cDNA in a Bacterial Expression System A segment in the central portion of the Mi-2 cDNA (nt 1422–2909) (FIGS. 1 and 2) was provided at the 5' end with an NdeI restriction site and at the 3' end with six histidine codons as well as a BamHI restriction site and, following ligation into the bacterial expression vector pET3b, transformed into E. coli BL21(DE3) pLysS. Studier et al., 1990, Methods Enzymol. 185:60–89. Following the culturing up to an $OD_{60}$ of 0.5, it was induced with 1 mM isopropyl-β-D-thiogalactopyranoside, further cultured for 8 hours and harvested. The cell pellet was suspended in 10 mM Tris-HCl (pH 8.0), 0.1 M sodium phosphate and 8 M urea, and the insoluble material which included the recombinant protein was obtained by centrifugation and dissolved in 8 M urea, 6 M guanidinium-HCl and obtained by means of $Ni^{2+}$ chelate affinity chromatography (Quiagen). The yield was about 200 mg of recombinant protein (rMi-2) per liter of culture. Following evaluation in SDS-PAGE, the size of the Mi-2 antigen corresponded to the derived molecular weight of 55 kD. All of the twelve anti-Mi-2-positive sera from dermatomyositis patients reacted in immunoblots with the rMi-2 antigen (FIG. 6, lane A2, TABLE I).

G. Example 7 rMi-2-Specific Human and Rabbit Sera and Anti-Mi-2 Sera React with the Same Natural Nuclear Protein Human anti-Mi-2-positive sera (Nos. 1, 2, 9 in TABLE I) and rabbit anti-rMi-2 sera were affinity-purified with rMi-2 antigens immobilized at nitrocellulose membranes. Both antibodies reacted not only with the rMi-2 antigen but also with epitopes of a natural HEp-2 cell nuclear proteins having an $M_r$~235 kD (FIG. 6). The 235 kD HEp-2 cell nuclear protein reacted in the immunoblot also with most of the anti-Mi-2-positive patient sera. Since both the human and the rabbit anti-rMi-2 immunoglobulines recognized the same nuclear protein as the patient sera, the 218 kD Mi-2 protein represents the main antigen of Mi-2. Differences existing between the molecular weight (M) calculated on the basis of the DNA sequence and the molecular weight ($M_r$) measured by means of SDS-PAGE, as in Mi-2 antigen, are observed frequently.

H. Example 8

Indirect Immunofluorescence Microscopy

All human anti-Mi-2 sera produced a characteristic finely granular nuclear fluorescence by means of HEp-2 cells, in some cases without dyeing the nucleoli. The antibody titers ranged between 1:160 and 1:5120 (FIG. 9, A1, TABLE I). An identical nuclear immunofluorescence pattern was observed with a human anti-Mi-2-positive serum after affinity purification with rMi-2 protein and with the rabbit anti-rMi-2 immunoglobulin.

TABLE I

Test Data of Patients Having Anti-Mi-2-Positive-Sera, Obtained by ELISA, Immunoblot, Immunoprecipitation or Immunodiffusion*

| | ANA Titer | Immunoblot | | Immunoprecipitation | ELISA | | |
|---|---|---|---|---|---|---|---|
| | HEp-2 Cells rez. ver. | rMi-2 rez. ver. | nat. Mi-2 rez. ver. | $^{35}$S-methionine HEp-2 cells | r-Mi-2 OD | Immuno-diffusion | Diagnosis |
| 1 | 5120 | 12800 | 3200** | 235 kD pos | 1.7 | + | DM |
| 2 | 1280 | 800 | <200 | 235 kD pos | 0.9 | + | DM |
| 3 | 2560 | 12800 | 12800 | 235 kD pos | 2.2 | + | DM |
| 4 | 5120 | 3200 | 800 | 235 kD pos | 1.7 | + | DM |
| 5 | 5120 | 3200 | 3200 | 235 kD pos | 1.6 | + | DM |
| 6 | 2560 | 400 | <200 | 235 kD pos | 0.8 | + | DM |
| 7 | 2560 | 3200 | 200 | 235 kD pos | 1.4 | + | DM |
| 8 | 320 | 3200 | 800 | 235 kD pos | 2.1 | + | DM |
| 9 | 2560 | 3200 | 200 | 235 kD pos | 1.7 | + | DM |
| 10 | 1280 | 3200 | 800 | 235 kD pos | 1.4 | + | DM |
| 11 | 160 | 400 | <200 | 235 kD pos | 0.4 | + | DM |
| 12 | 1280 | 12800 | 12800 | 235 kD pos | 2.3 | + | DM |

TABLE I-continued

Test Data of Patients Having Anti-Mi-2-Positive-Sera, Obtained by ELISA, Immunoblot, Immunoprecipitation or Immunodiffusion*

| | ANA Titer | Immunoblot | | Immunoprecipitation | ELISA | | |
|---|---|---|---|---|---|---|---|
| | HEp-2 Cells rez. ver. | rMi-2 rez. ver. | nat. Mi-2 rez. ver. | 35S-methionine HEp-2 cells | r-Mi-2 OD | Immuno- diffusion | Diagnosis |
| 13 | 20480 | 1600 | 200 | 235 kD pos | 0.8 | + | SLE, anti-dsDNA positive |
| 14 | 5120 | 200 | <200 | 235 kD pos | 0.7 | ND | non-def. collagen disease |
| 15 | 320 | 400 | <200 | 235 kD pos | 0.6 | ND | proteinuria, thyroiditis |

*Nos. 1–12 Comprise patients having defined DM, Nos. 13–15 represent three patients of the ANA positive group (n = 901), rMi-2: recombinant Mi-2 antigen fragment (SEQ ID NO: 1 aa474-969, encoded by nt1422-2909; see Example F); nat. Mi-2: major antigen (218 kD Mi-2 antigen, SEQ ID NO: 2) having an electrophoretic migration, corresponding to 235 kD, detected by ani-Mi-2 positive sera in immunoblots of nuclear proteins separated by SDS-PAGE; rez. ver.: reciprocal serum dilutions.
Immunoprecipitation: carried out with 35S-methionine-labeled HEp-2 cell extract.
Precipitation of a 235 kD nuclear protein with epitopes cross-reacting with the 218 kD Mi-2 antigen.
ND: not investigated.

I. Example 9

ELISA for Determining Anti-218 kD Mi-2 Antibodies in Patient Sera

Microtiter plates (Immunolon, Dynatech, Denkendorf) were incubated per recess with 100 µl of a solution consisting of 8 µg/ml rMi-2 antigen and 0.1 M sodium carbonate (pH 9.6) at 4° C. for 16 hours and then blocked per recess with 300 µl of a solution consisting of PBS and 0.1% BSA at 4° C. for 16 hours. Antibody screening was carried out with 200 µl of serum per recess (serum dilutions: 1:300 in PBS, 0.01% Tween and 0.1% BSA) at 37° C. during 30 minutes of incubation. After a wash step (5×PBS, 0.01% Tween, at 37° C. for 30 minutes) each recess was incubated with 200 µl of a peroxidase-labeled rabbit anti-human IgG F(ab')$_2$ with 1:2000 dilution in PBS, 0.01% Tween and 0.5% BSA at 37° C. for 30 minutes and washed again. Bound antibodies were visualized with OPD, and the enzyme reaction was stopped with 50 µl 4 M H$_2$SO$_4$ per recess. The absorption was measured bichromatically at 492/20 nm. 1368 human sera were tested with this assay (FIG. 10). The mean OD value of a control group of 189 healthy persons was 0.25±0.08: ODs between 0.5 and 0.6 were evaluated to be limiting values, ODs>0.6 were considered positive. The antibody concentrations (ODs) of the twelve anti-Mi-2-positive dermatomyositis patients are listed in FIG. 11. With the exception of one serum, which was negative in the ELISA but positive in the immunoblot assay, all patient sera showed OD values markedly above the limiting value.

All references cited within the body of the instant specification are hereby incorporated by reference in their entirety.

What is claimed:

1. An isolated polypeptide comprising a polypeptide as shown in SEQ ID NO:2.

2. An isolated polypeptide encoded by a polynucleotide selected from the group consisting of:
   (a) a polynucleotide consisting of the sequence as shown in SEQ ID NO:1 from nucleotide number 1422 through nucleotide number 2909;
   (b) a polynucleotide consisting of the sequence as shown in SEQ ID NO:1 from nucleotide number 153 through nucleotide number 4902;
   (c) a polynucleotide consisting of the sequence as shown in SEQ ID NO:1 from nucleotide number 649 through nucleotide number 4891;
   (d) a polynucleotide consisting of the sequence as shown in SEQ ID NO:1 from nucleotide number 1931 through nucleotide number 4881;
   (e) a polynucleotide consisting of the sequence as shown in SEQ ID NO:1 from nucleotide number 2204 through nucleotide number 4888;
   (f) a polynucleotide consisting of the sequence as shown in SEQ ID NO:1 from nucleotide number 3224 through nucleotide number 4888;
   (g) a polynucleotide consisting of the sequence as shown in SEQ ID NO:1 from nucleotide number 3620 through nucleotide number 4888;
   (h) a polynucleotide consisting of the sequence as shown in SEQ ID NO:1 from nucleotide number 3666 through nucleotide number 6155;

(i) a polynucleotide consisting of the sequence as shown in SEQ ID NO:1 from nucleotide number 3843 through nucleotide number 6239; and (j) a polynucleotide consisting of the sequence as shown in SEQ ID NO:1 from nucleotide number 3967 through nucleotide number 6155.

3. An isolated polypeptide selected from the group consisting of:

(a) a polypeptide consisting of the sequence as shown in SEQ ID NO:2 from amino acid residue number 54 through amino acid residue number 74;

(b) a polypeptide consisting of the sequence as shown in SEQ ID NO:2 from amino acid residue number 114 through amino acid residue number 134;

(c) a polypeptide consisting of the sequence as shown in SEQ ID NO:2 from amino acid residue number 134 through amino acid residue number 144;

(d) a polypeptide consisting of the sequence as shown in SEQ ID NO:2 from amino acid residue number 258 through amino acid residue number 288;

(e) a polypeptide consisting of the sequence as shown in SEQ ID NO:2 from amino acid residue number 748 through amino acid residue number 759;

(f) a polypeptide consisting of the sequence as shown in SEQ ID NO:2 from amino acid residue number 783 through amino acid residue number 794;

(g) a polypeptide consisting of the sequence as shown in SEQ ID NO:2 from amino acid residue number 870 through amino acid residue number 878;

(h) a polypeptide consisting of the sequence as shown in SEQ ID NO:2 from amino acid residue number 898 through amino acid residue number 911;

(i) a polypeptide consisting of the sequence as shown in SEQ ID NO:2 from amino acid residue number 944 through amino acid residue number 960;

(j) a polypeptide consisting of the sequence as shown in SEQ ID NO:2 from amino acid residue number 950 through amino acid residue number 961;

(k) a polypeptide consisting of the sequence as shown in SEQ ID NO:2 from amino acid residue number 1122 through amino acid residue number 1145; and (l) a polypeptide consisting of the sequence as shown in SEQ ID NO:2 from amino acid residue number 1150 through amino acid residue number 1184.

4. An isolated polypeptide encoded by a polynucleotide that hybridizes at 20° C. below the DNA melting point to the complement of:

(a) a polynucleotide consisting of the sequence as shown in SEQ ID NO:1 from nucleotide number 1422 through nucleotide number 2909;

(b) a polynucleotide consisting of the sequence as shown in SEQ ID NO:1 from nucleotide number 153 through nucleotide number 4902;

(c) a polynucleotide consisting of the sequence as shown in SEQ ID NO:1 from nucleotide number 649 through nucleotide number 4891;

(d) a polynucleotide consisting of the sequence as shown in SEQ ID NO:1 from nucleotide number 1931 through nucleotide number 4881;

(e) a polynucleotide consisting of the sequence as shown in SEQ ID NO:1 from nucleotide number 2204 through nucleotide number 4888;

(f) a polynucleotide consisting of the sequence as shown in SEQ ID NO:1 from nucleotide number 3224 through nucleotide number 4888;

(g) a polynucleotide consisting of the sequence as shown in SEQ ID NO:1 from nucleotide number 3620 through nucleotide number 4888;

(h) a polynucleotide consisting of the sequence as shown in SEQ ID NO:1 from nucleotide number 3666 through nucleotide number 6155;

(i) a polynucleotide consisting of the sequence as shown in SEQ ID NO:1 from nucleotide number 3843 through nucleotide number 6239; or (j) a polynucleotide consisting of the sequence as shown in SEQ ID NO:1 from nucleotide number 3967 through nucleotide number 6155;

wherein said isolated polypeptide binds to an autoantibody from a dermatomyositis patient.

5. An isolated polypeptide encoded by a polynucleotide that hybridizes at 20° C. below the DNA melting point to the complement of a polynucleotide encoding the amino acid sequence of SEQ ID NO:2 wherein said isolated polypeptide binds to an autoantibody from a dermatomyositis patient.

* * * * *